US006227053B1

United States Patent
Purpura et al.

(10) Patent No.: US 6,227,053 B1
(45) Date of Patent: May 8, 2001

(54) DYNAMIC NONINVASIVE DETECTION OF ANALYTICAL CONTAINER FEATURE USING ULTRASOUND

(75) Inventors: Paul E. Purpura, Yorktown; Ralph Waters, Washingtonville, both of NY (US); Olivier Landier, Paris (FR); Beri Cohen, Hartsdale, NY (US)

(73) Assignee: Bayer Corporation, Tarrytown, NY (US)

( * ) Notice: Subject to any disclaimer, the term of this patent is extended or adjusted under 35 U.S.C. 154(b) by 0 days.

(21) Appl. No.: 09/115,393

(22) Filed: Jul. 14, 1998

(51) Int. Cl.[7] .............................. G01N 29/00; G01F 23/00

(52) U.S. Cl. ........................................... 73/627; 73/290 V

(58) Field of Search .................................. 73/290 V, 627, 73/628, 629, 290 R

(56) References Cited

U.S. PATENT DOCUMENTS

| 5,088,328 | * | 2/1992 | John, Jr. et al. ........................ 73/622 |
| 5,507,178 | | 4/1996 | Dam . | |
| 5,793,705 | * | 8/1998 | Gazis et al. ............................ 367/98 |
| 5,880,364 | * | 3/1999 | Dam ...................................... 73/149 |
| 5,996,407 | * | 12/1999 | Hewitt ................................ 73/290 V |

OTHER PUBLICATIONS

Cosense—Installation / Operation Manual for ML–102 Ultrasonic Micro Measurement System—Cosense Inc. Hauppage, NY (12 pp.).

* cited by examiner

Primary Examiner—Richard A. Moller
(74) Attorney, Agent, or Firm—Andrew L. Klawitter; John M. Paolino

(57) ABSTRACT

A profile of a rack, that may have zero, one, or a plurality of containers may be obtained using an ultrasonic sensor. The sensor emits a plurality of ultrasonic bursts and the rack is transported under the sensor at a slew speed that allows the sensor to detect at least first and second echoes from each of the bursts. Data points, corresponding to each of the first and second echoes, are generated and the data points are captured in a memory device. The data points, generally reflecting the levels of the rack and any containers, are processed to dynamically and non-invasively (i.e., without physically contacting the liquid with a probe) determine information about the container types, whether any container is capped, and, if one or more containers are uncapped, the liquid level in the uncapped containers. This profiling may be used in a variety of devices and is particularly useful in a sample handler in an automated analytical instrument, where the ultrasonic sensor may be positioned above a rack transport mechanism.

19 Claims, 22 Drawing Sheets

Microfiche Appendix Included
(1 Microfiche, 88 Pages)

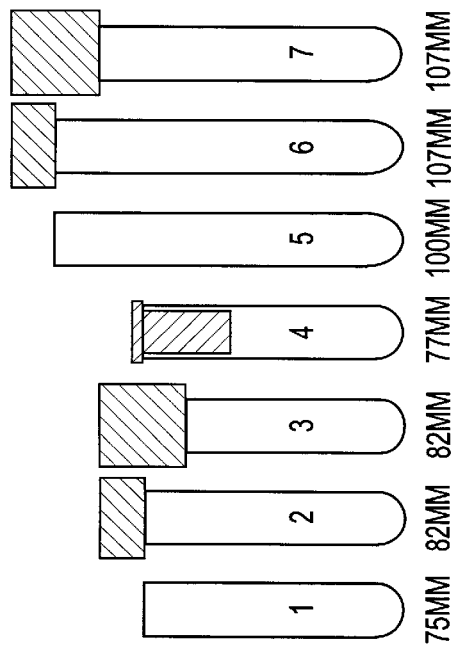
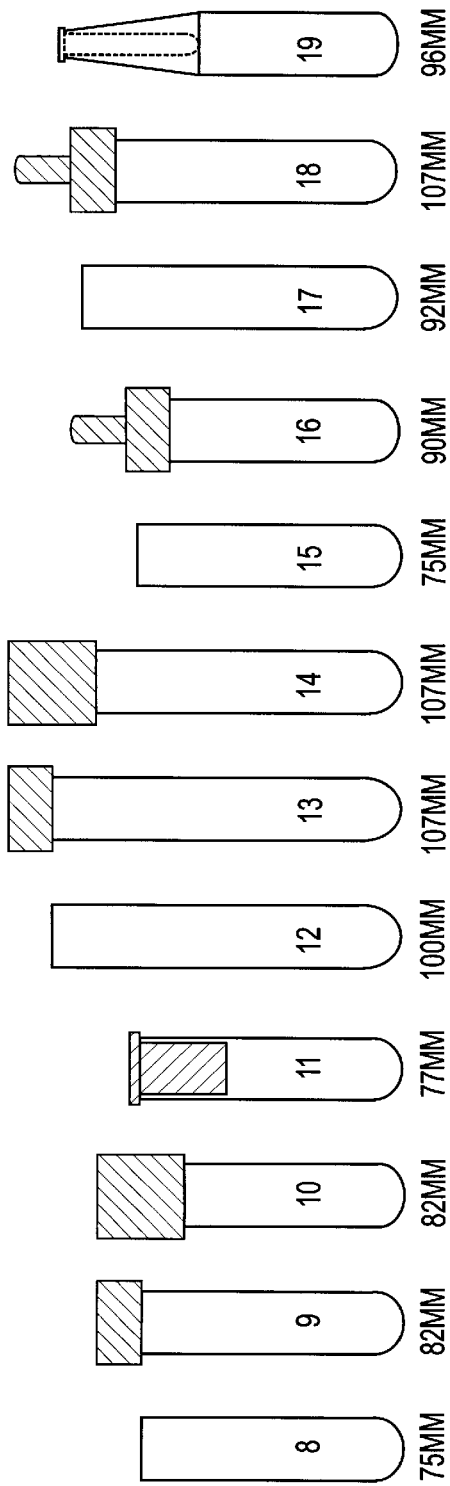
FIG. 1

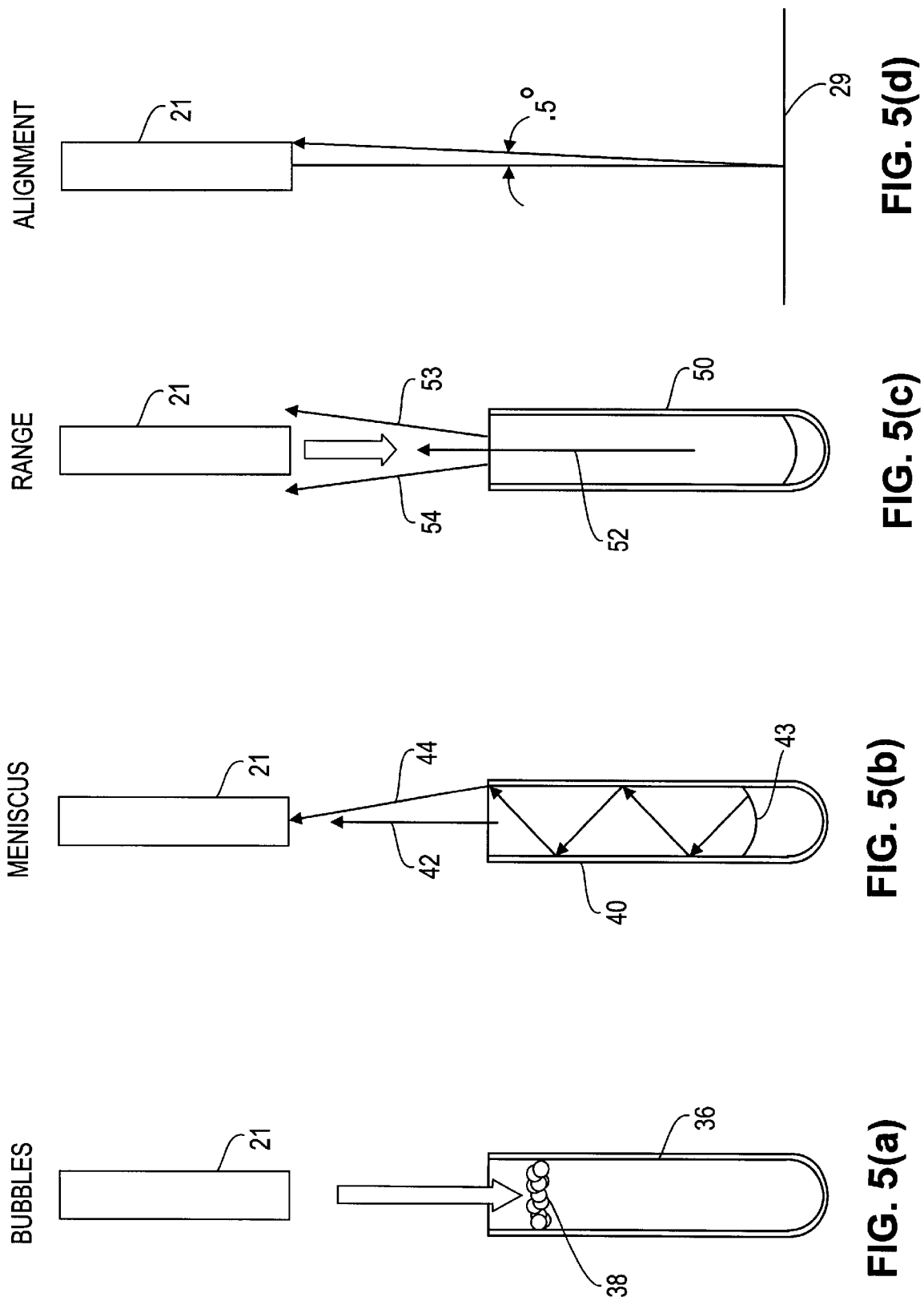

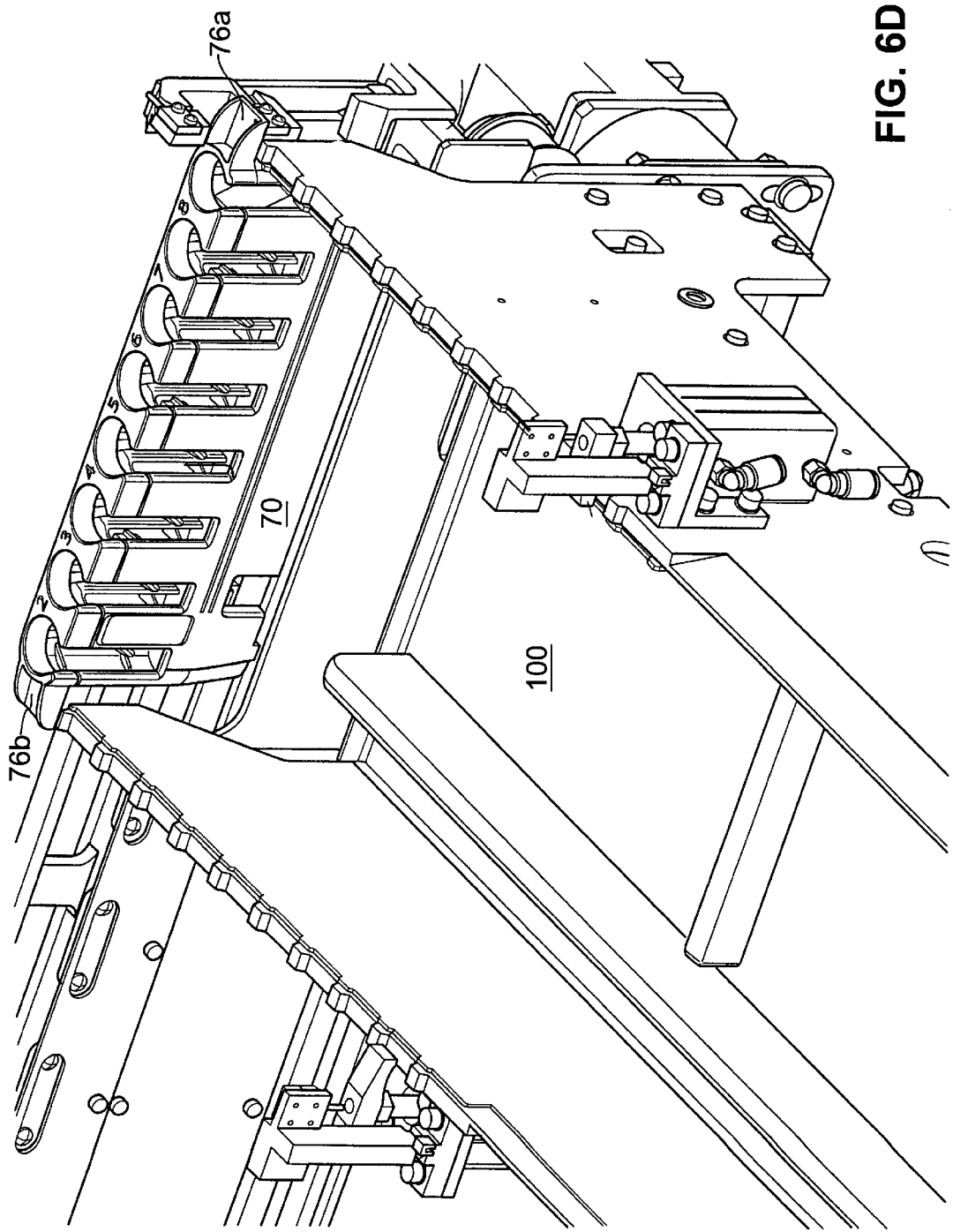

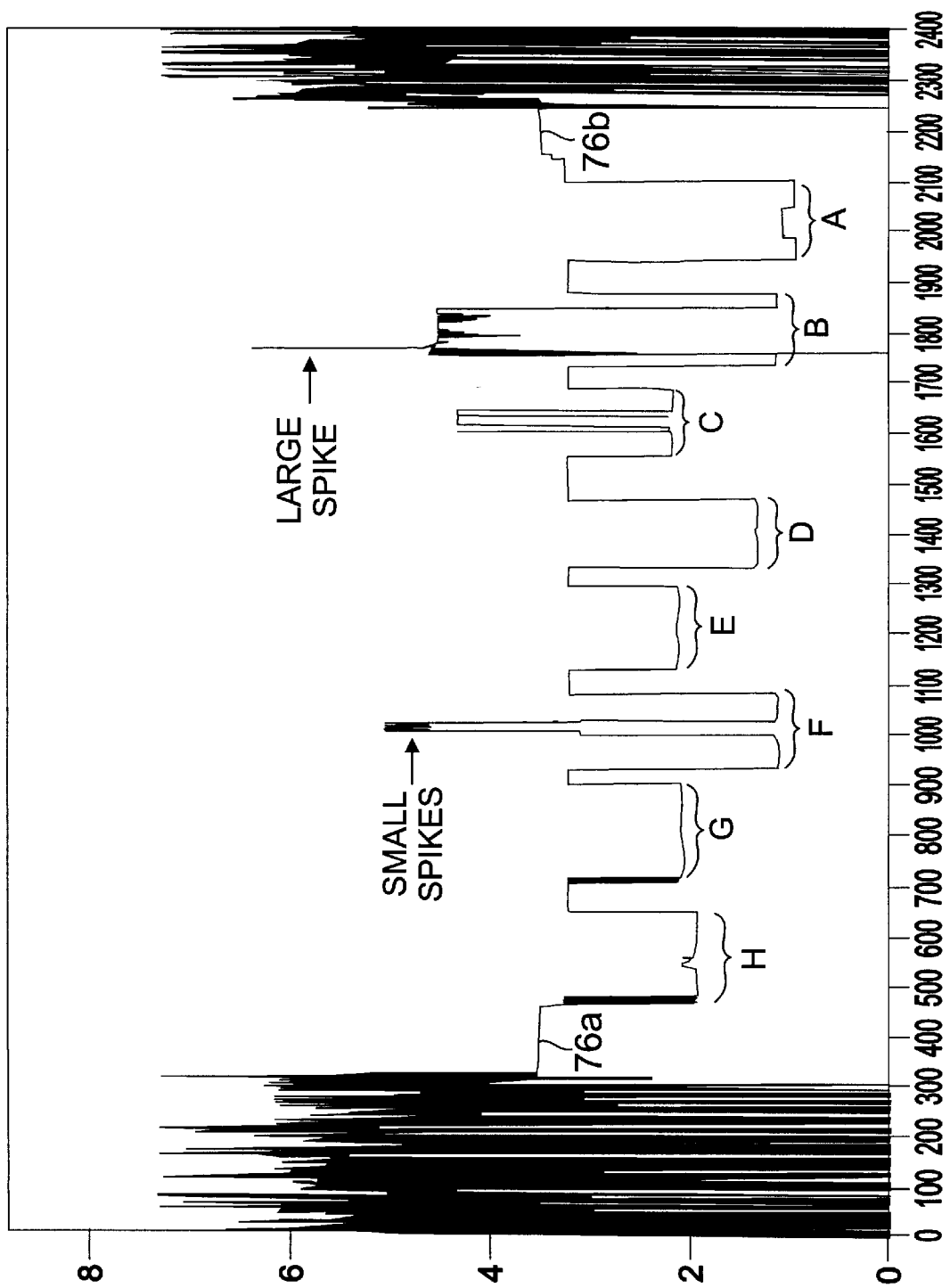

DYNAMIC NONINVASIVE DETECTION OF ANALYTICAL CONTAINER FEATURE USING ULTRASOUND

CROSS-REFERENCE TO RELATED APPLICATIONS

This application is related to the following U.S. patent applications, having the indicated titles, which are commonly-assigned to the Bayer Corporation of Tarrytown, N.Y. and are incorporated by reference herein:

Utility patent applications for Robotics for Transporting Containers and Objects within an Automated Analytical Instrument and Service Tool for Servicing Robotics Ser. No. 09/115,080, filed concurrently herewith; Automatic Handler for Feeding Containers Into and Out of An Analytical Instrument ("Sample Handler"), Ser. No. 09/115,391, filed concurrently herewith; Sample Tube Rack, Ser. No. 09/097, 790, filed Jun. 15, 1998; Reagent Package, Ser. No. 08/985, 759, filed Dec. 5, 1997; Diluent Package, Ser. No. 29/088, 045, filed May 14, 1998; Stat Shuttle Adapter and Transport Device, Ser. No. 09/113,640, filed Jul. 10, 1998; Automatic Decapper, Ser. No. 09/115,777, filed concurrently herewith; and Cup Handling Subsystem for an Automated Clinical Chemistry Analyzer System Ser. No. 09/099,738, filed Jun. 18, 1998.

MICROFICHE APPENDIX

A Microfiche Appendix is attached hereto and forms a part of this application. The Microfiche Appendix includes 1 microfiche with a total of 88 frames.

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

1. Field of the Invention

This invention relates to the profiling of containers using an ultrasonic liquid level sensor to detect a series of data points that are processed to determine information about the containers, such as container type, whether the container is capped, and, if the container is not capped, the liquid level in the containers.

2. Background of the Invention

A variety of different types and sizes of test tubes and inserts (such as Ezee Nest® tubes that are inserted into ordinary Vacutainer® test tubes or sample cups that are inserted into Microtainer® holders), generically "containers" (or "vessels"), are currently in use in laboratories and hospitals throughout the world. However, there are only a few such containers that comprise the majority of containers in use. These include the Vacutainer® test tubes and Microtainer® holders, both manufactured by the Becton-Dickinson Corporation, test tubes from Sarstedt of Germany, and the two types of inserts mentioned above: Ezee Nest® inserts and Microtainer® holders. Other test tubes are manufactured by Braun of Germany, Meditech, Inc. of Bel Air, Md., and Greiner, among others. The below discussion refers to the Vacutainer® and Sarstedt test tubes and the inserts but would apply equally to other test tubes and other containers as long as sufficient information is provided to the workstation software for the system to identify the containers and distinguish them from other containers.

The Vacutainer® test tubes are available in 4 sizes, 13 mm (diameter)×75 mm (height), 13 mm×100 mm, 16 mm×75 mm, and 16 mm×100 mm. All of these Vacutainer® test tubes may be capped with a rubber stopper or a rubber Hemoguard® cap. The test tubes that are 75 mm in height may alternatively have an Ezee Nest® insert, which holds a small amount of a sample, inserted into the top of the Vacutainer® test tube to be supported by the lip of the test tube. The Sarstedt test tubes are available in two sizes: 16 mm×75 mm and 16 mm×92 mm and may be capped with unique twist-on caps. The other referenced test tubes likewise have unique features, such as size, that are sufficient to identify them.

Some of the various types of containers referred to above are shown in FIG. 1. The containers are numbered 1–19 and identified in the identification key on FIG. 1. The maximum height of each container is listed below the figure of that container. The listed height includes the height of the container plus any additional height due to the height of the cap or insert.

It is important to be able to process the different types of containers in an automated analytical instrument while requiring as little human intervention, such as data entry of information about the containers, as possible. It would therefore be useful to have an analytical instrument that dynamically determines the container type and liquid level in the container. Similarly, the instrument should also be able to detect capped test tubes in order to know which test tubes must be automatically decapped at an automatic decapping area of the instrument before further processing of the test tubes.

It is further desirable to maximize the throughput of the analytical instrument. One way to maximize throughput is to minimize the downward travel of a probe for aspirating liquid samples from the containers by maximizing the speed with which the probe may be lowered. The probe must enter the liquid slowly so as not to enter the liquid surface at a high velocity, which would perturb the hydraulic interface at the probe tip. If the liquid level in each container is known before the probe is lowered, the probe may be quickly lowered to slightly above the liquid level and a capacitive liquid level sensor on the tip of the probe may be used to lower the probe the additional small distance necessary to enter the sample. This speeds up the cycle time in which each sample is aspirated, as otherwise the probe would have to be lowered at a steady, slow rate until the probe determines the liquid level. To lower the probe more quickly requires a specific acceleration/deceleration motion profile determined by the location of the top surface of the liquid.

An ultrasonic sensor may be used to detect objects not in contact with the sensor. (FIG. 2) The ultrasonic sensor comprises a transducer 21 with a piezoelectric tip mounted in a sensor holder 20. Transducer 21 alternates between operating as a transmitter and receiver. When operating as a transmitter, an electrical pulse is applied to transducer 21, causing transducer 21 to ring at a particular ultrasonic frequency, which is in the range of approximately 50 kHz to 2 MHz. Transducer 21 rings freely until it eventually stops ringing. The ringing transmits an ultrasonic burst, represented by arrow 23, for a length of time that is dependent on the pulse width applied to transducer 21 and the size of transducer 21.The ultrasonic burst has a greater amplitude when initially generated and then attenuates over time. (FIG. 4) The burst propagates through air toward a targeted surface, such as surface 22, and, when it strikes the targeted surface, at least a portion of the wave which is not absorbed by the surface, if any, is reflected back toward sensor 21 as one or more echoes 24. The sensor is able to detect the echoes after it has finished ringing and is switched to a receive mode.

The ultrasonic burst propagates as a cone-shaped wave. Referring to FIG. 3, where a first surface 25 has an aperture 26, the burst will impinge upon the first surface 25 and pass through the aperture 26 to impinge on a second lower surface 29, if any. The burst is reflected back from the first, closer surface 25 as a first echo 27 and from the second, farther surface 29 as a second echo 28, which arrives at sensor 21 after the first echo 27. The time it takes for each ultrasonic burst to travel from sensor 21 and to return back to sensor 21 as one or more echoes is captured in memory. Software, known to those skilled in the art and typically included by the sensor manufacturer in a printed wire assembly (referred to below as a data acquisition board) which is designed to operate with the sensor, then converts the time measurements to measurements of the distance which the ultrasonic bursts have traveled using the known speed of sound (which equals 331.36 m/sec at ambient temperature).

An ultrasonic sensor may be used in a variety of applications to take measurements over a wide range of distances. They may be used as short range sensors to take measurements as close as a few centimeters away from the sensor or as long range sensors to take measurements as far away as a few meters. Ultrasonic sensors have typically been used in applications such as detecting and identifying solid objects, measuring the shape and orientation of a workpiece, detecting possible collisions between objects to avoid the collisions, room surveillance, flow measurement, and determining a type of material by measuring the absorption of sound.

Ultrasonic liquid level sensing is a known process that uses an analog ultrasonic sensor to measure the level of liquid in a container without physically contacting the liquid. One such sensor that may be used for ultrasonic liquid level sensing is described in U.S. Pat. No. 5,507,178 assigned to Cosense, Inc. of Hauppauge, N.Y. Cosense also manufactures an ultrasonic micro measurement system ML-102, which may be used for liquid level sensing. Ultrasonic sensors are better suited for liquid level sensing in narrow containers than optical sensors because they are at most nominally affected by dust, may be used over a wide range of distances, are inexpensive, and light does not interfere with the measurements. The Cosense sensor has been used by the Becton-Dickinson Corporation for determining the level of liquid in Micro pipette trays that are statically placed underneath the sensor.

It is also known in the prior art that information regarding the profile of vehicles passing a toll booth may be collected using an ultrasonic low frequency broad beam long range sensor, which is far less precise than an ultrasonic liquid level sensor, to determine the volume and types of vehicles, such as whether it is a car or truck, passing a particular toll booth. The sensor takes a number of readings, collecting data points to create a profile of the vehicles. Obviously, the precise model or manufacturer of the vehicle is unimportant in this situation and an imprecise profile containing data points which are not processed further to obtain precise measurements may be used to provide the required information.

SUMMARY OF THE INVENTION

It is therefore an object of this invention to provide a method of using an ultrasonic sensor that transmits an ultrasonic beam focused downward on a moving rack of containers to profile the rack and containers and thereby determine information about them, which may include the type and size of the container, whether the container is capped, and, if the container is not capped, the liquid level in the containers.

The present invention is directed to a method of profiling one or more containers in a rack using the ultrasonic sensor. The rack is transported within a sensing range of the sensor, in particular, by transporting the rack with a rack transport mechanism, such as a cross-feed or shuttle, under the ultrasonic sensor at a slew speed, while the ultrasonic sensor transmits a plurality of ultrasonic bursts toward the rack. As the sensor may be used to profile relatively small containers, the sensor is preferably operated as a short range sensor with bursts emitted at a frequency of 1 MHz. The sensor detects echoes generated by the ultrasonic bursts striking the rack and the containers as the rack is transported past the sensor and these echoes are detected. The first and second echoes generated by each of the bursts are captured and processed to profile the containers. Using the detected echoes, a processor generates data points indicating the distance the echoes traveled in a single direction before being reflected back to the ultrasonic sensor. These data points are saved in a memory device associated with the ultrasonic sensor and are processed to profile the container.

BRIEF DESCRIPTION OF THE DRAWINGS

The inventions and modifications thereof will become better evident from the detailed description below in conjunction with the following figures, in which like reference characters refer to like elements, and in which:

FIG. 1 is an elevational view of some of the various types of containers that may be profiled;

FIG. 5(*a*) is a front elevational view of the ultrasonic liquid level sensor emitting an ultrasonic wave into a container containing liquid with bubbles at the upper surface of the liquid;

FIG. 5(*b*) is a front elevational view of the ultrasonic liquid level sensor emitting an ultrasonic wave into a container where a meniscus has formed within the test tube;

FIG. 5(*c*) is a front elevational view of a container that is positioned outside of the range of the ultrasonic liquid level sensor;

FIG. 5(*d*) is a front elevational view of an ultrasonic liquid level sensor that is misaligned;

FIG. 6D is an isometric view of the rack after it is transported across the cross-feed to a position behind the outfeed;

FIG. 7A is a graph of the ultrasonic profile of the raw data for the first echo generated by profiling a rack having the indicated containers;

DETAILED DESCRIPTION OF THE PREFERRED EMBODIMENT

Figure 6A:
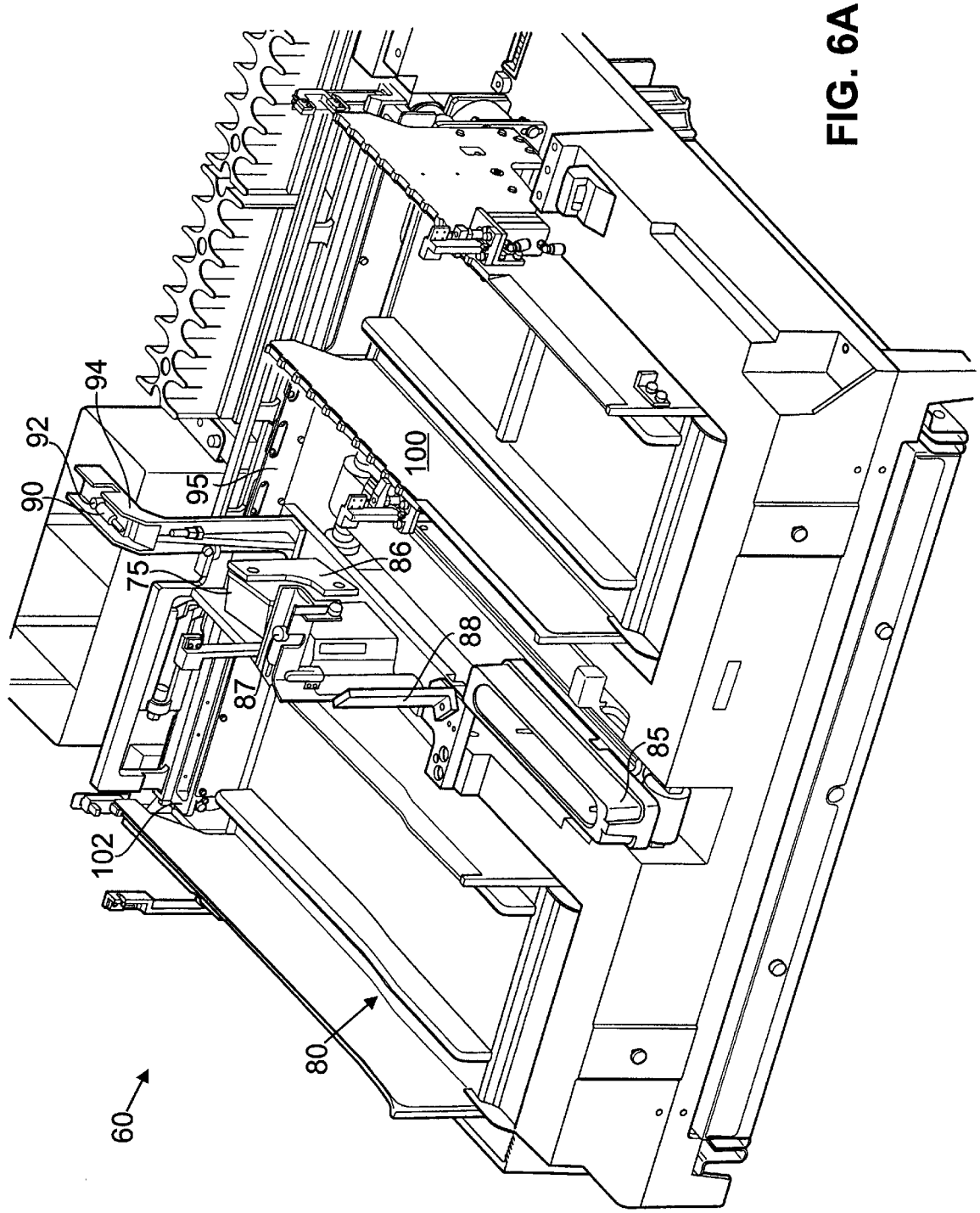
FIG. 6A is an isometric view of the sample handler that includes the ultrasonic liquid level sensor.
Figure 6B:
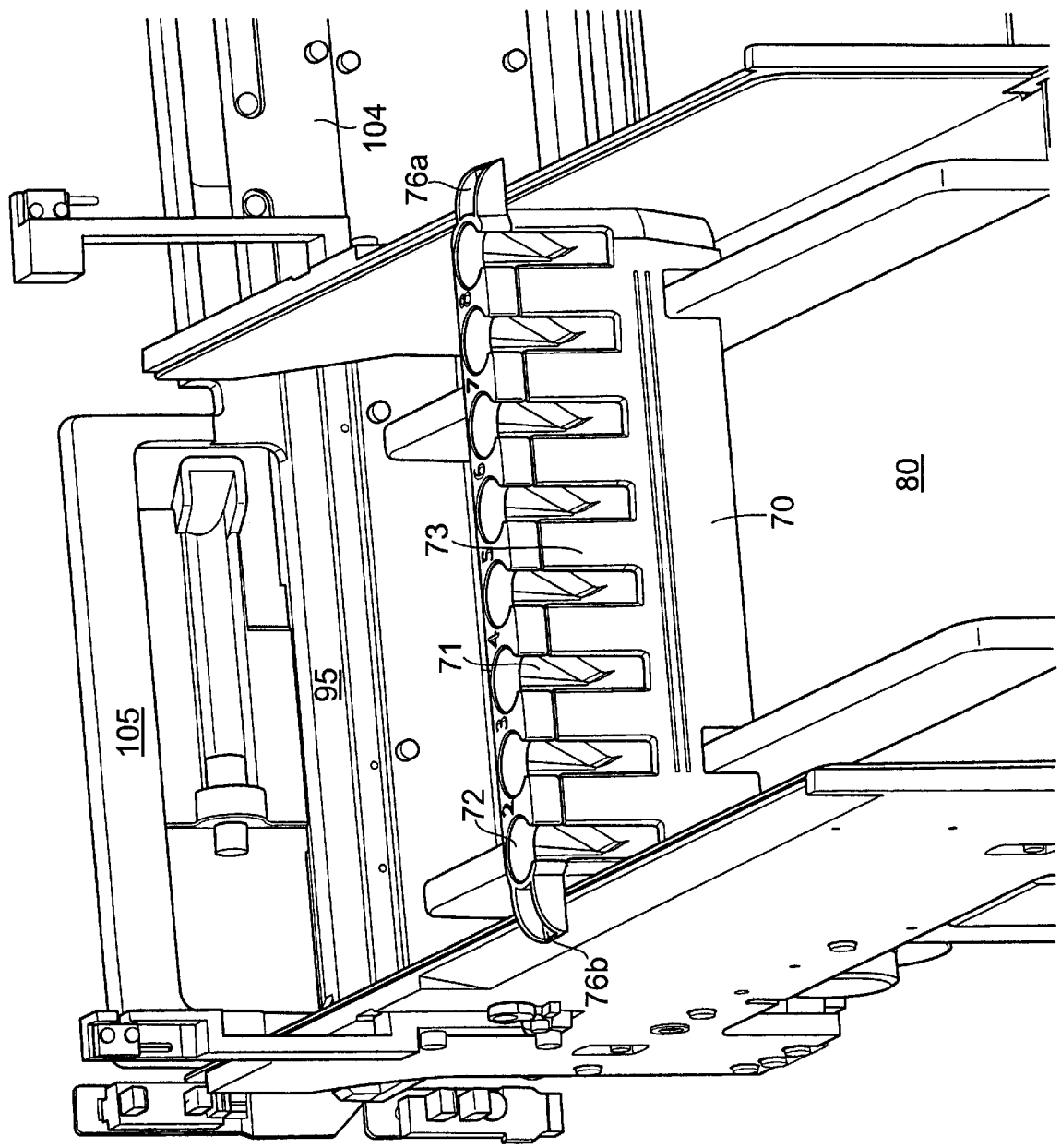
FIG. 6B is an isometric view of a first embodiment of a rack with which this invention may be used positioned in the infeed of the sample handler.
Figure 6C:
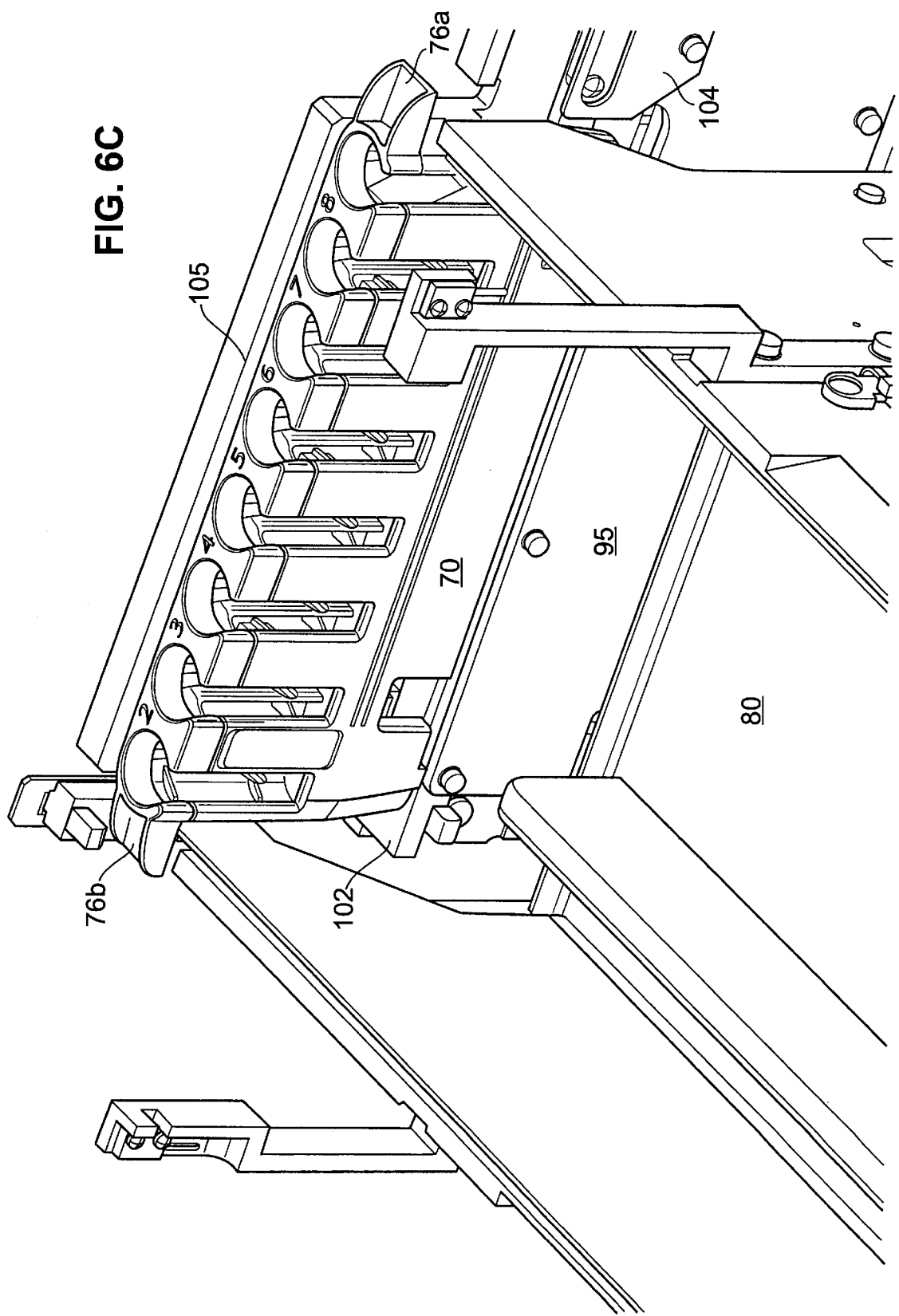
FIG. 6C is an isometric view of the rack transferred from the infeed to a position on the cross-feed behind the infeed.

Referring to FIG. 6A, an automated sample handler 60 for an analytical instrument, such as the sample handler described in the referenced Sample Handler application, feeds containers into the instrument. The sample handler may be part of a single instrument or may be a single module in a modular instrument comprising modules for analysis of the samples and for processing the samples before analysis. Sample handler 60 comprises an infeed 80, a cross-feed 95 (or "cross-feed shuttle") and an outfeed 100. Racks 70 (FIG. 6B), such as those described in the referenced application assigned Internal Docket No. MST-2302, are used to transport the containers within sample handler 60. Sample handler 60 has a master controller (not shown), such as a controller based on an Intel 386EX microprocessor, to control the operations of sample handler 60.

Racks 70 of containers are inserted into infeed 80 and are transferred one at a time to a track 102 on cross-feed 95 positioned behind infeed 80 and outfeed 100. The containers inserted into the racks 70 may include one or more containers of one of the 19 container types shown in FIG. 1. However, as indicated above, any container that has unique features identifiable by profiling and whose identifying features are saved in workstation software may be inserted into sample handler 60 and profiled by the ultrasonic profiling of the present invention. (In certain circumstances, a completely empty rack with no containers may be inserted.). A transport mechanism (not shown) in cross-feed 95 engages the rack 70 and pushes it from the infeed side to the outfeed side of cross-feed 95 and holds it in place there while the containers may be extracted from the rack by a robotic arm moving overhead to be fed elsewhere in the instrument. (FIG. 6D) The rack 70 is then output into outfeed 100. After the other modules in instrument have completed their operations on the containers, the containers are returned by the robotic arm to the racks 70 in outfeed 100 for removal from sample handler 60.

Each of racks 70 may hold as many as eight containers of the various types and sizes, including the 19 types shown in FIG. 1, in individual tube receptacles 72 that are equally spaced and separated by side walls 74. Each tube receptacle 72 within rack 70 has a diameter large enough for containers of various diameters nominally between 8 mm and 16 mm to be placed therein. Each rack 70 has a machine-readable identification code, such as a bar code label, to identify the rack 70 and each container also has a machine readable identification code. Containers are placed in the rack 70 by the operator who must firmly seat the containers in tube receptacles 72 with the identification code of the containers visible through openings 71 in a lateral front wall 73 of each rack 70. A bar code reader 75 (or, if a machine readable identification code other than bar codes are used, a device suitable for reading that code) and an ultrasonic liquid level sensor 90 are positioned along the middle section of cross-feed 95 between infeed 80 and outfeed 100. The rack 70 with containers first passes the bar code reader 75, which is on the side of cross-feed 95 between infeed 80 and outfeed 100, where the bar codes on the rack 70 and containers are read and the data is transmitted to the sample handler controller to both identify each rack and container and to determine the number of containers in the rack 70. Further along cross-feed 95, the rack 70 passes under ultrasonic liquid level sensor 90 positioned above cross-feed. (FIG. 6E) Rack 70 is transported in cross-feed 95 at a preferred slew speed of approximately 2 inches/sec to allow a sufficient number of data points for the profiling to be taken.

A bidirectional stat shuttle 85 may also be included on sample handler 60, such as between infeed 80 and outfeed 100, to input test tubes on a priority basis or when infeed 80 is broken. (FIG. 6A) Stat shuttle may also be used to input other containers, such as reagent or diluent packages, for use by the instrument and to output the test tubes and other containers. Like cross-feed 95, stat shuttle 85 has a bar code reader 86 and ultrasonic liquid level sensor 87 positioned adjacent stat shuttle 85 to perform the same operations when the containers are fed into the sample handler 60 via the stat shuttle 85. Due to space constraints, bar code reader 86 may be mounted behind sensor 87 and reads the bar code via a mirror 88.

Tabs (or "ears") 76*a*, 76*b* on each side of racks 70 are located at the top of racks 70 at the same height on each side of racks 70. Tabs 76*a*, 76*b* are used for various purposes including to hold racks 70 upright and to lift and advance the position of the rack 70 in infeed 80 and outfeed 100 as explained below. Of particular importance to the present invention, tabs 76*a*, 76*b* provide a reference level for the profiling described below. In one preferred embodiment, racks 70 are approximately three inches high and approximately 228 mm long from the outer end of one tab to the outer end of the other tab. One skilled in the art will understand that the racks 70 may vary in size and the algorithms provided below may be adjusted accordingly to accommodate the exact rack configuration.

Figure 6E:
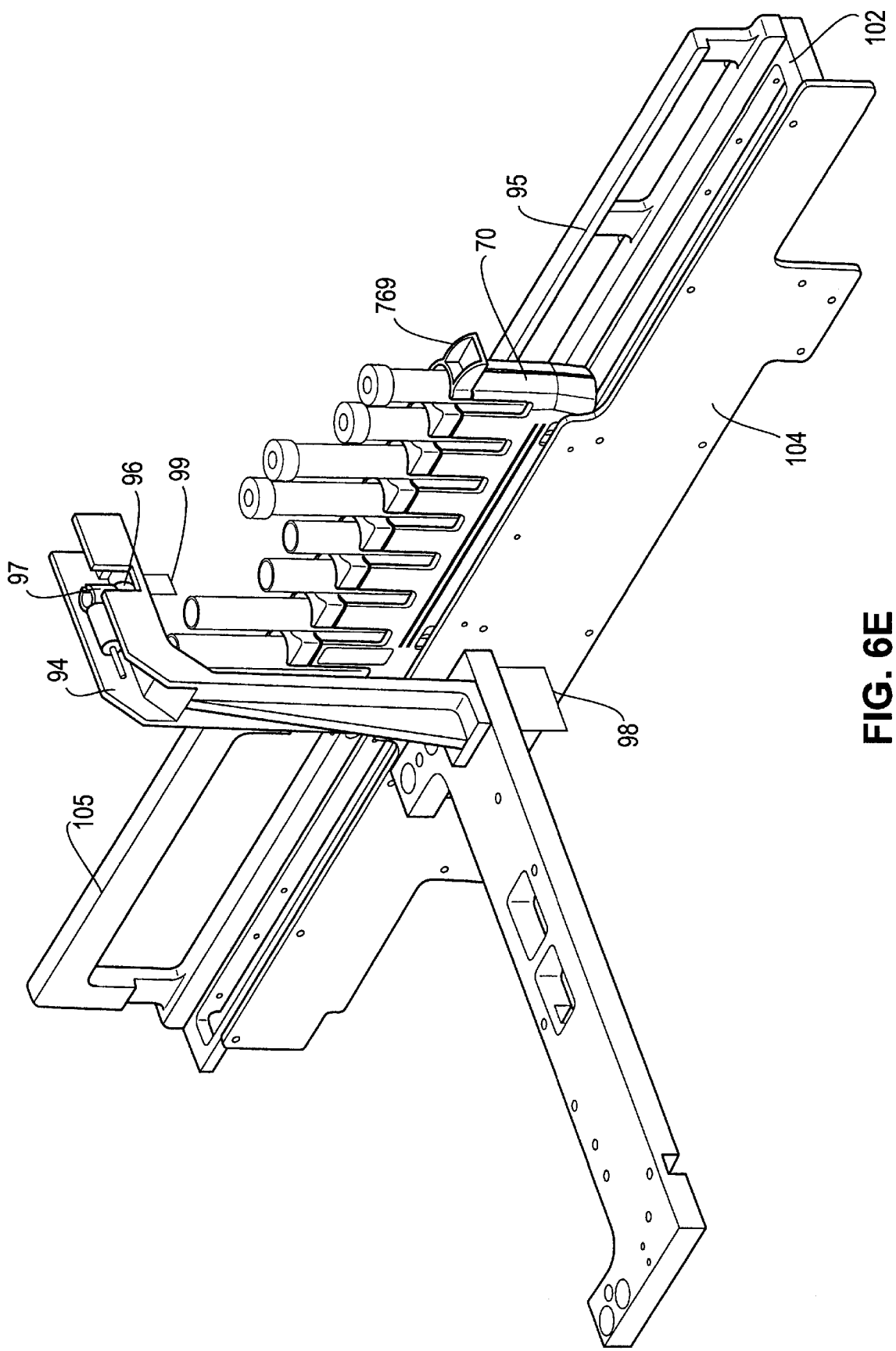
FIG. 6E is an isometric view of the ultrasonic level sensor mounted in a sensor holder above a shuttle that transports a rack of containers beneath the ultrasonic level sensor.
Figure 6F:
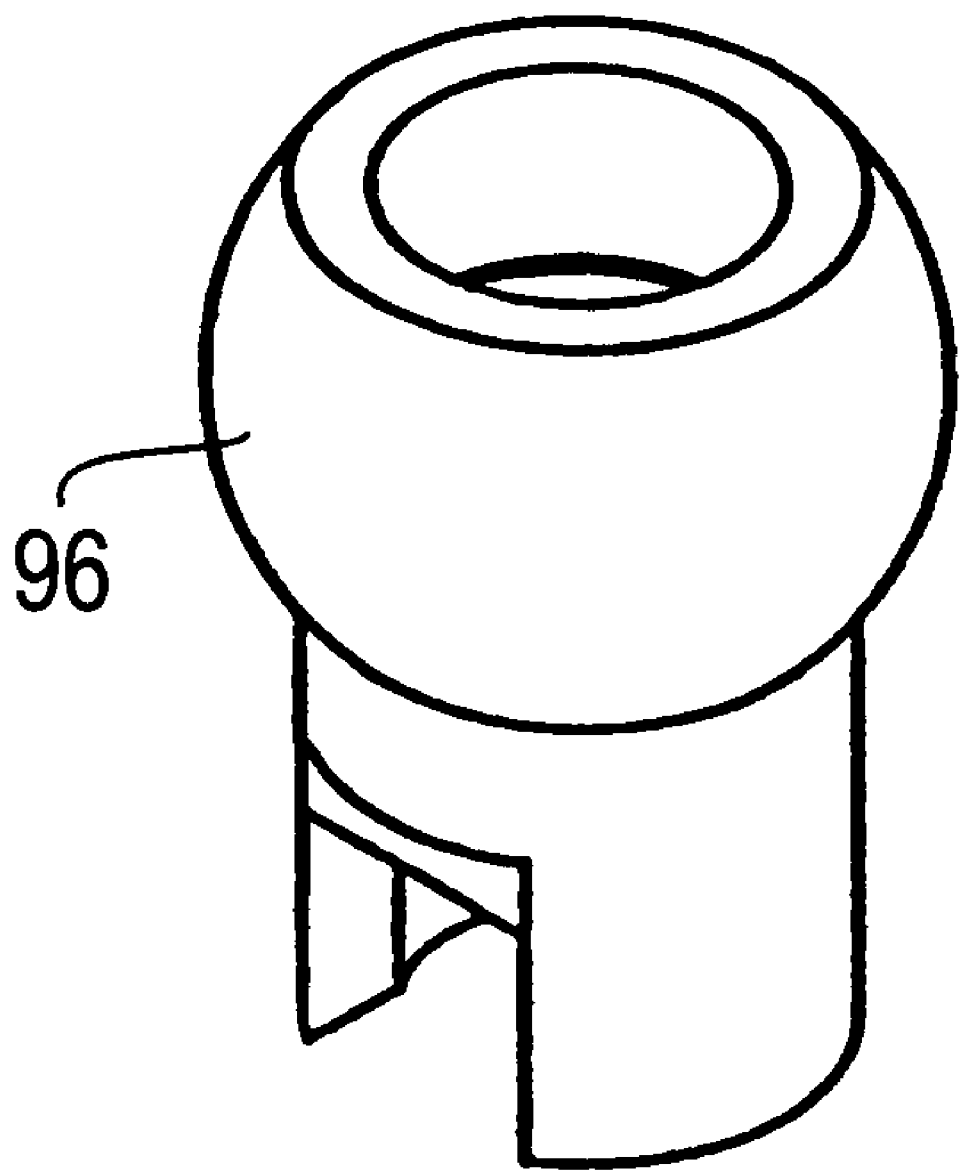
FIG. 6F is an isometric view of the gimbal to be mounted within a sensor holder.

Ultrasonic liquid level sensor 90 is preferably mounted in a sensor holder 92 mounted to the top of an L-shaped bracket 94 (FIG. 6B) that overhangs cross-feed 95. Sensor holder 92 has a non-metallic gimbal 96 (FIG. 6F) that permits sensor 90 to be adjusted to point perpendicularly to the top of the target on the rack 70. The precise alignment of gimbal 96 is achieved with a jig (not shown) that is similar to rack 70. A tube pin is pressed through gimbal 96, a tube receptacle on the jig, and the aperture within track 102, thereby causing gimbal 96 to self-align. After gimbal 96 is adjusted, it is locked in place with two set screws 97 (FIG. 6E). The tube pin is then removed and sensor 90 is placed within gimbal 96.

Sensor 90 is held by sensor holder 92 above the transducer 99 so as not to interfere with the ringing of a transducer 99 with or limit the beam shape of the ultrasonic burst. To prevent the need to realign sensor 90 after servicing instrument, bracket 94 preferably pivots backward on a hinge (not shown) when a screw that holds the bracket down is removed to allow a technician to work on the system. A data acquisition board 98 is mounted near bracket 94 as well. Board 98 communicates with the sample handler controller.

Ultrasonic liquid level sensor 90 must be able to detect surfaces within a short range from sensor 90. While sensor 90 is ringing, it is unable to receive and detect echoes. Therefore, there is a region adjacent sensor 90 through which the ultrasonic burst propagates before sensor 90 is able to detect echoes. This region is a dead zone where echoes reflected from a surface in this region will not be detected at sensor 90.

In a preferred embodiment, sensor 90 is preferably a Cosense sensor Part No. 123-10001. Sensor 90 has a transducer 99 that is 0.25 inches in diameter and approximately 0.75 inches in length. A pulse having a frequency of approximately 1.0 MHz and a pulse width of approximately 1 microsecond is applied to sensor 90, causing sensor 90 to ring possibly as long as, but not longer than, 100 microseconds. When operated within these parameters, sensor 90 has a dead zone of approximately 12.7 mm (=0.5 inches). The high ultrasonic frequency of 1.0 MHz is used (typically ultrasonic sensors are operated in the kHz range) to reduce the length of ringing of the transducer 99, thereby minimizing the size of the dead zone. For the same reason, sensor holder 92 is nonmetallic so as not to extend the length of time the transducer 99 rings.

Sensor 90 should be mounted in sensor holder 92 at a sufficiently high enough distance above the containers, (preferably between 0.65 and 1 inch) so that the tallest test tube which may have a cap on it does not extend into the dead zone where it would go undetected by sensor 90 (as explained further below). Sensor 90 must also be able to detect liquid levels to the bottom of the containers. Leaving 1 inch between the dead zone and the tallest test tube and with the sensor 90 having the given dimensions and operated at the specified frequency yields a sensing range of approximately 5 inches. To accommodate the required sensing range, sensor 90 should be mounted approximately 5 inches above the lowest point on which the container will rest. If a container passes outside of the sensing range of sensor 90, as shown in FIG. 5(c), nothing will be sensed and an error code will be generated.

Sensor 90 must be properly aligned in bracket 94 such that the ultrasonic burst will be precisely directed downward toward the center of each container. If sensor 90 is misaligned more than 2 degrees, the echoes generated by the ultrasonic burst will be reflected back and forth between the side walls of the containers, as shown in FIG. 5(d), and will therefore take much longer than appropriate to return to sensor 90. In this event, the container may be either misidentified and the liquid level misread, rejected as unrecognizable, or not detected at all.

Rack 70 must also be aligned with sensor 90 or the rack may be the source of misalignment problems. Therefore, the track 102 on cross-feed 95 must be level and the engagement mechanism on the bottom of the rack 70, which engages the rack to the transport mechanism rack, must maintain the rack 70 flush with the track 102 as it moves under sensor 90. The front and rear walls 104, 105 of cross-feed 95 also assist in maintaining the perpendicularity of the rack on track 102 by preloading the front of the rack 70 against the rear wall 105 of cross-feed 95.

Figure 2:
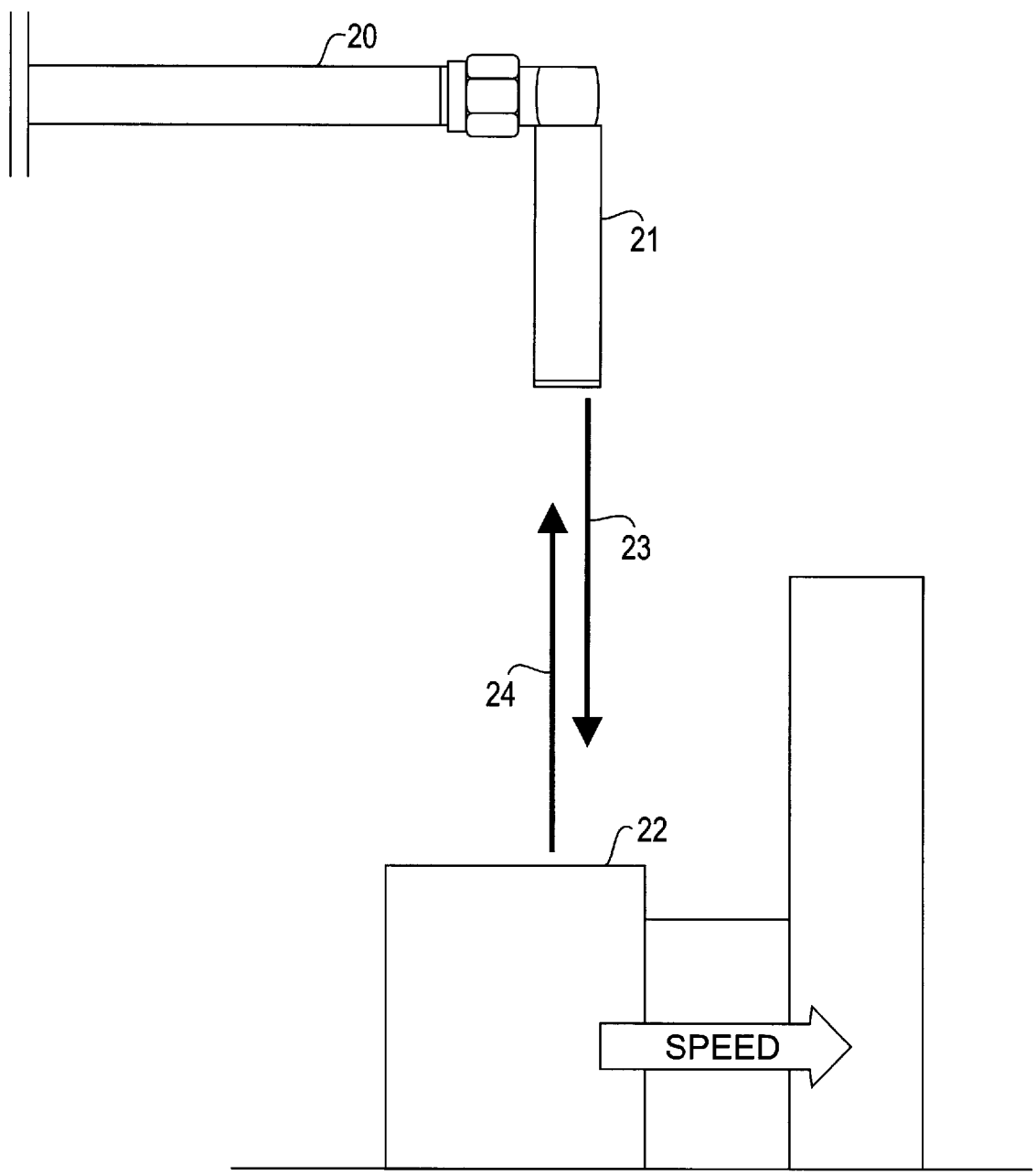
FIG. 2 is an elevational side view of an ultrasonic liquid level sensor according to the invention transmitting an ultrasonic wave directed toward a container and receiving a first echo back from the container.
Figure 4:
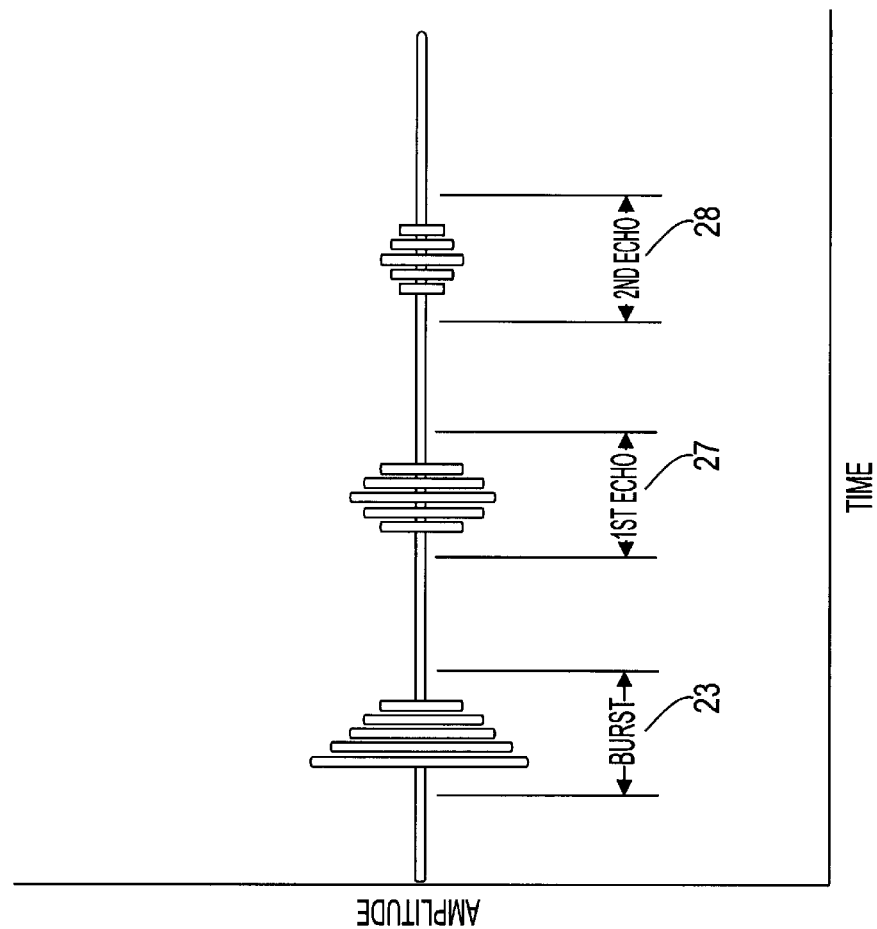
FIG. 4 is a graph plotting distance versus time of the ultrasonic burst and the first and second echoes.
Figure 3:
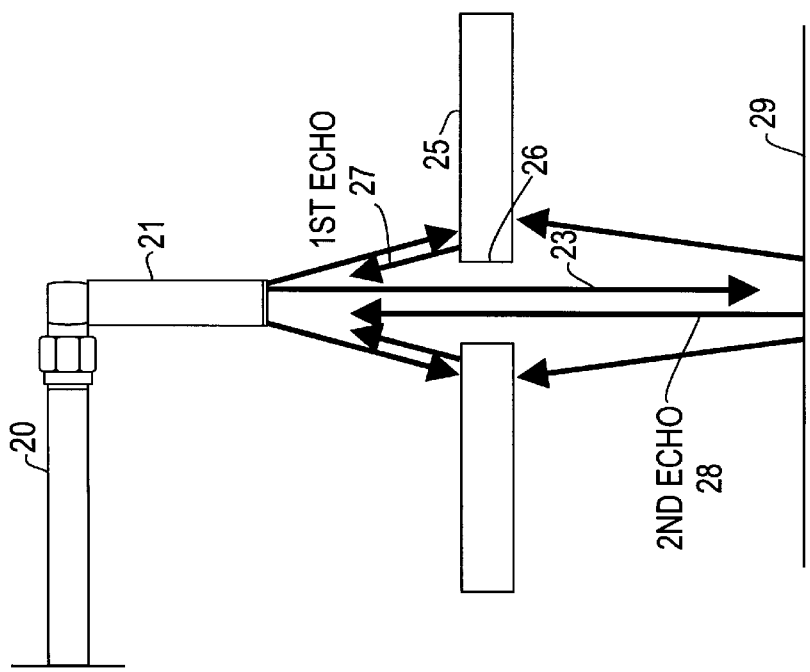
FIG. 3 is an elevational side view of the ultrasonic liquid level sensor of FIG. 2 transmitting an ultrasonic wave directed toward a container, such as a MICROTAINER or EZEE-NEST container, and the first and second echoes reflected back toward the sensor.

While detecting the first echo may be sufficient to profile certain containers, it is advantageous to also capture the second echoes generated by the ultrasonic burst to obtain certain information not provided by the first echoes. The information provided by the second echo is especially important where there is a large difference between the distance which the first and second echoes must travel, as when narrow containers such as the Ezee-Nest® inserts and MICROTAINER sample cups are profiled. As will be understood from FIG. 3, where the ultrasonic burst impinges on narrow apertures, such as the apertures on certain containers, the first echo is reflected off the curved lip at the top of the narrow VACUTAINER test tube or MICROTAINER holder relatively quickly while the second echo is generated by the sample, which is much farther down. Taking the first echo profile only, therefore, would profile the container as having a flat top and no liquid level would be determined.

Figure 11:
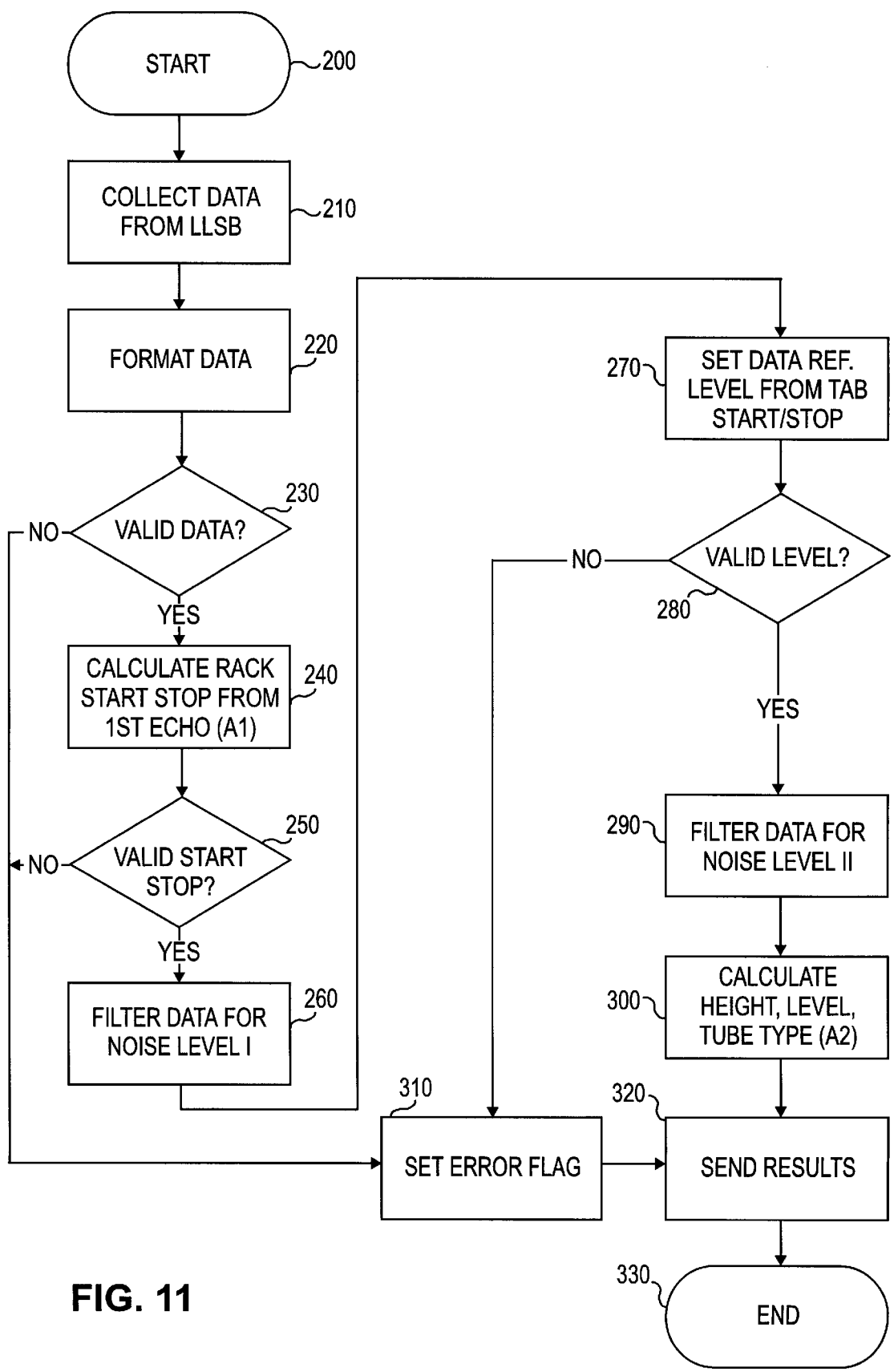
FIG. 11 is a flow chart of algorithm for profiling a test tube rack and any test tubes or inserts in the rack.

The profiling of the rack 70 and containers in the rack 70 is performed using an algorithm initiated by software in the sample handler controller. Source code for the preferred profiling algorithm is contained in the attached Microfiche Appendix and FIG. 11 is a flow chart of the algorithm, which starts at step 200. At step 210, data points are collected as the rack 70 moves along cross-feed 95. Starting from the rest position behind infeed 80, the rack 70 in cross-feed 95 accelerates up to a slew speed of 2 inches/sec, which must remain as constant and smooth as possible while rack 70 passes under sensor 90 for sensor 90 to read the level of data points, which are equally spaced from one another along the length of the rack 70. Sensor 90 is activated by the sample handler controller when the rack transport mechanism is activated to move the rack 70 on cross-feed 95. Sensor 90 emits one ultrasonic burst for approximately 1 microsecond every 2.5 milliseconds. As explained, the ultrasonic burst rings for no longer than 100 microseconds. During this time, no signal can be detected and sensor 90 is in a "Window Closed" condition. After the 100 microsecond burst is completed, sensor 90 switches to a receive mode, referred to as a "Window Open" condition, for approximately 900 microseconds to detect first and second echoes of the ultrasonic burst that are reflected back to sensor 90.

Empty receptacles appear as levels of 0 inch height. This, coupled with the detection of a container wall, determines whether a no container or empty container condition is detected.

With sensor 90 in the "Window Open" condition, sensor 90 thereafter takes continuous readings approximately every 2.5 ms, which equals approximately one reading every $5/1000$ of an inch or 200 times per inch along the length of the rack.

The values of the readings ("data points") are saved in a FIFO buffer on the data acquisition board 98, such as the board made by Cosense Model No. MIL-101, which communicates with sensor 90 via an RS-232 serial port. (MIL-101 is a single channel board that only accepts data from a single ultrasonic sensor. A multichannel board for simultaneously reading data from multiple ultrasonic sensors may alternatively be used.) Data is saved in the FIFO buffer in the format of MMMMM NNNNN, where MMMMM and NNNNN are five digit ASCII fixed point values. MMMMM is the value in inches at which the first echo was reflected back to sensor 90 and NNNNN is the value in inches at which the second echo was reflected back to sensor 90. For example, where MMMMM equals 02345 and NNNNN equals 04567, this indicates that the first echo was reflected back to sensor 90 at 2.345 inches away from sensor 90 and the second echo was reflected back to sensor 90 at 4.567 inches away from the sensor 90. Alternatively, data may be saved in the FIFO buffer in a binary or another format.

Sensor 90 turns off after reading 2400 data points, which should be a more than sufficient number of data points to profile the entire rack 70. The reasoning for requiring 2400 data points is as follows: Rack is 228 mm long and, since there are approximately 200 readings per inch, there will be approximately 1795 significant data points comprising 1795 readings by sensor 90 per rack (=(228 mm/25.4 mm/inch)× 200 readings/inch) contained within the complete set of readings captured by the data acquisition board 98 for the time during which the rack is transported. The data points captured within a certain distance before and after the rack 70 has passed under sensor 90 are also significant as they provide the ability to detect the leading and trailing edges of the rack 70. While the minimum number of data points required between the leading and trailing edges is as close to the 1795 data points as possible, it has been found that it is advantageous to capture and save in the FIFO buffer a total of 2400 data points for the rack 70, which includes the 1795 points for the rack 70. This leaves 605 data points to capture data about the leading and trailing edges of the rack 70, or (605 data points/200 data point/inch/2 edges=1.51) as much as a total of approximately 1.51 inches per edge both before and after the rack 70. Taking these additional readings will assist in profiling as motor speeds and the starting and stopping accelerations of the transport mechanism in cross-feed 95, as the parameters cannot be precisely set in each instrument.

Figure 7B:
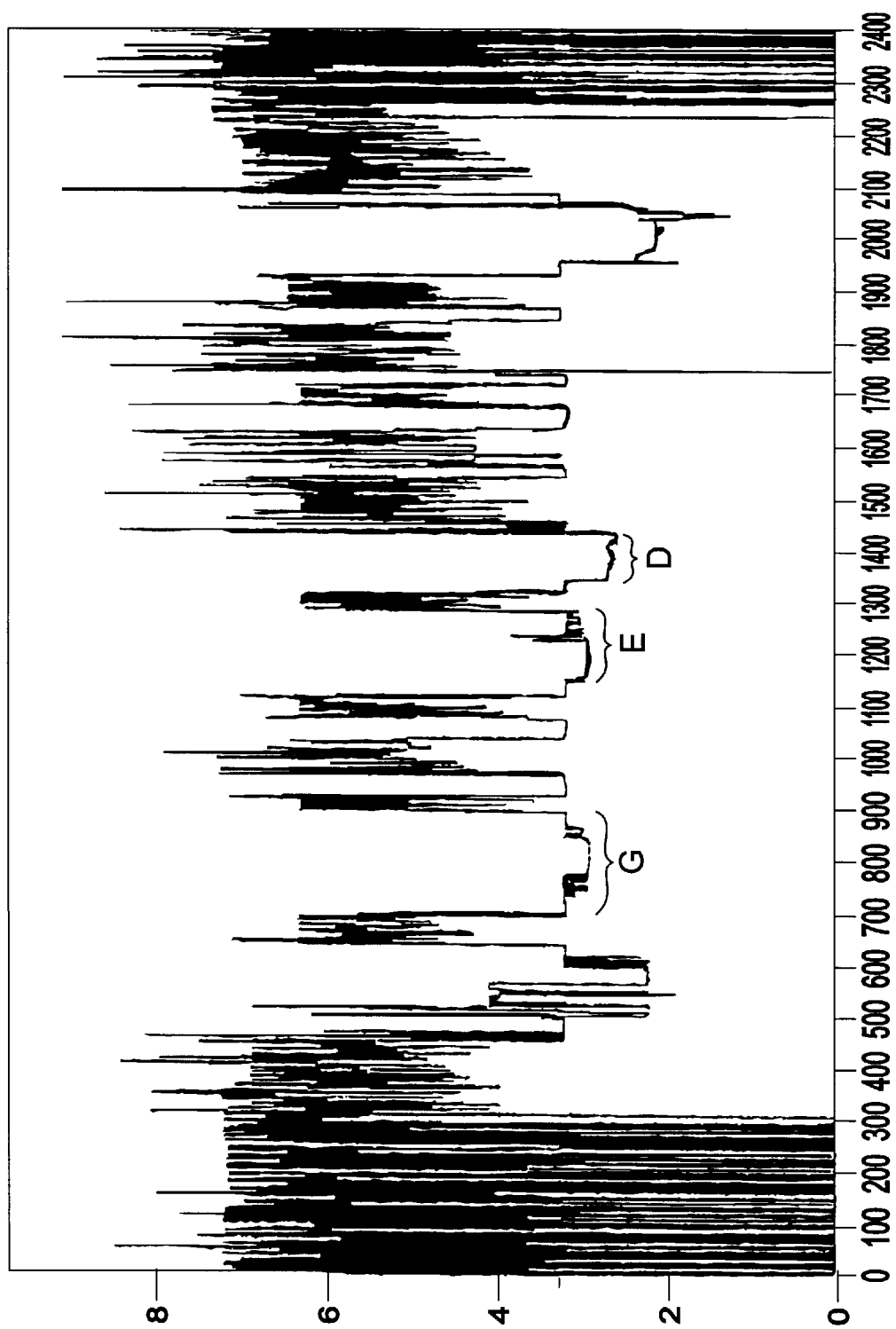
FIG. 7B is a graph of the profile of the raw data for the second echo generated by profiling the rack and containers of FIG. 7A.

Raw data for a first echo of one rack 70 having the containers indicated in Table I is shown in FIG. 7A. Raw data for a second echo of that rack is shown in FIG. 7B.

TABLE I

| AREA OF INTEREST | CONTAINER TYPE |
| --- | --- |
| A | 13 × 100 VACUTAINER - Capped |
| B | 13 × 100 VACUTAINER - Open |
| C | 13 × 75 VACUTAINER - Open |
| D | MICROTAINER |
| E | 13 × 75 VACUTAINER with EZEE-NEST insert |
| F | 13 × 100 VACUTAINER - Open |
| G | 16 × 75 VACUTAINER with EZEE-NEST insert |
| H | 16 × 75 VACUTAINER - Capped |

Figure 10A:
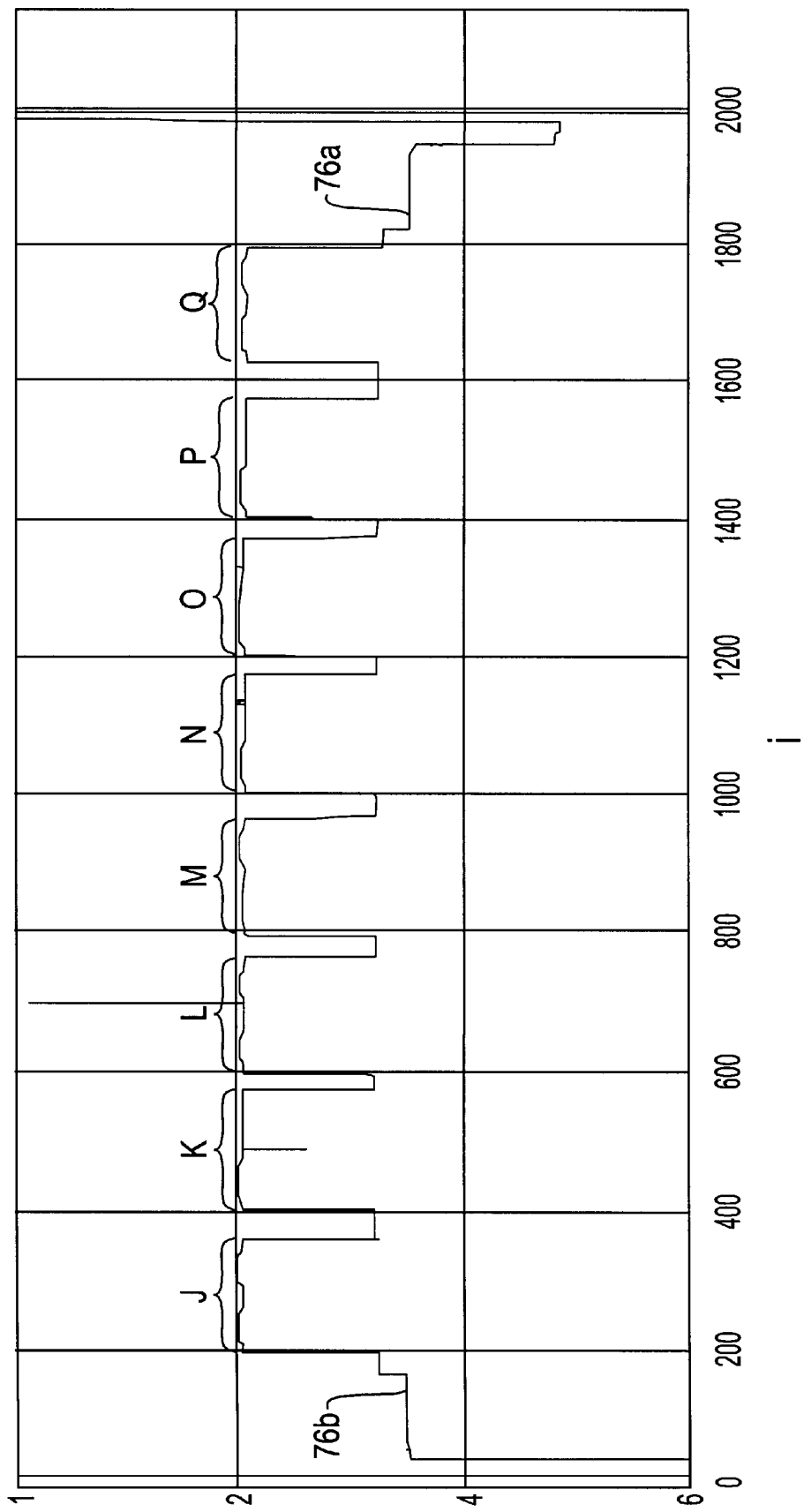
FIG. 10A is a graph of the ultrasonic profile of raw data for the first echo generated by profiling a rack having 75×100 VACUTAINER test tubes with EZEE-NEST inserts.
Figure 10B:
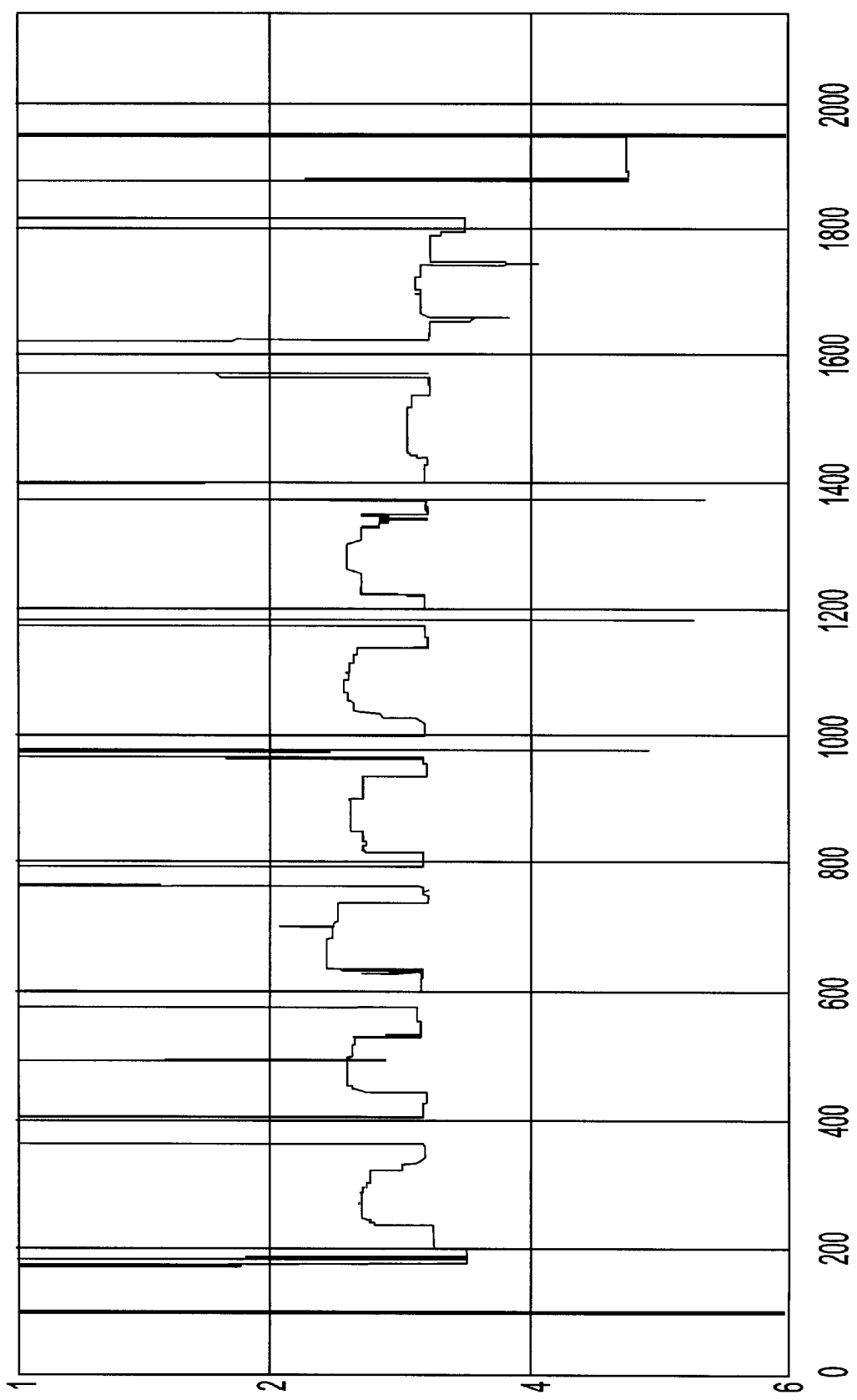
FIG. 10B is a graph of the profile of the raw data for the second echo generated by profiling the rack and containers of FIG. 7B.

Raw data for a first echo generated by a rack with eight 75×100 VACUTAINER test tubes with EZEE-NEST inserts is shown in FIG. 10A. Raw data for a second echo generated by this same rack and containers is shown in FIG. 10B.

At step 220, the entire set of raw data for the 2400 data points of interest is sent to the sample handler controller which processes the data, reformats the data from the MMMMM NNNNN format to an alternative appropriate format (such as 32 bit floating values), as dictated by the particular hardware, and the operating system and application software, and is saved to the FIFO buffer.

After 900 microseconds from the beginning of the first ultrasonic burst, sensor 90 again switches to the "Window Closed" condition and is ready to emit another ultrasonic burst. Because of the speed of sound, which at ambient temperature is 331.36 m/sec=1089 feet/sec=13068 inches/sec, the distance over which the ultrasonic burst may travel before it can be detected is 1.307 inches (at 100 microseconds) and the maximum distance at which it may be detected is 11.76 inches (at 900 microseconds). Since the burst must both travel and return during that period when there is a "Window Open" condition, the minimum and maximum distances the ultrasonic burst must travel to be detected is 0.65 inches (=1.307 inches/2 directions) and 5.88 inches (=11.76/2). The "Window Closed" condition is intentionally set to leave additional time for the ringing of sensor 90, even though sensor 90 should stop ringing after less than 100 microseconds and only have a dead zone of 0.5 inches. If an echo is not detected during this period, the echoes are lost and a zero value 00000 00000 is returned to the data acquisition board 98.

Figure 12:
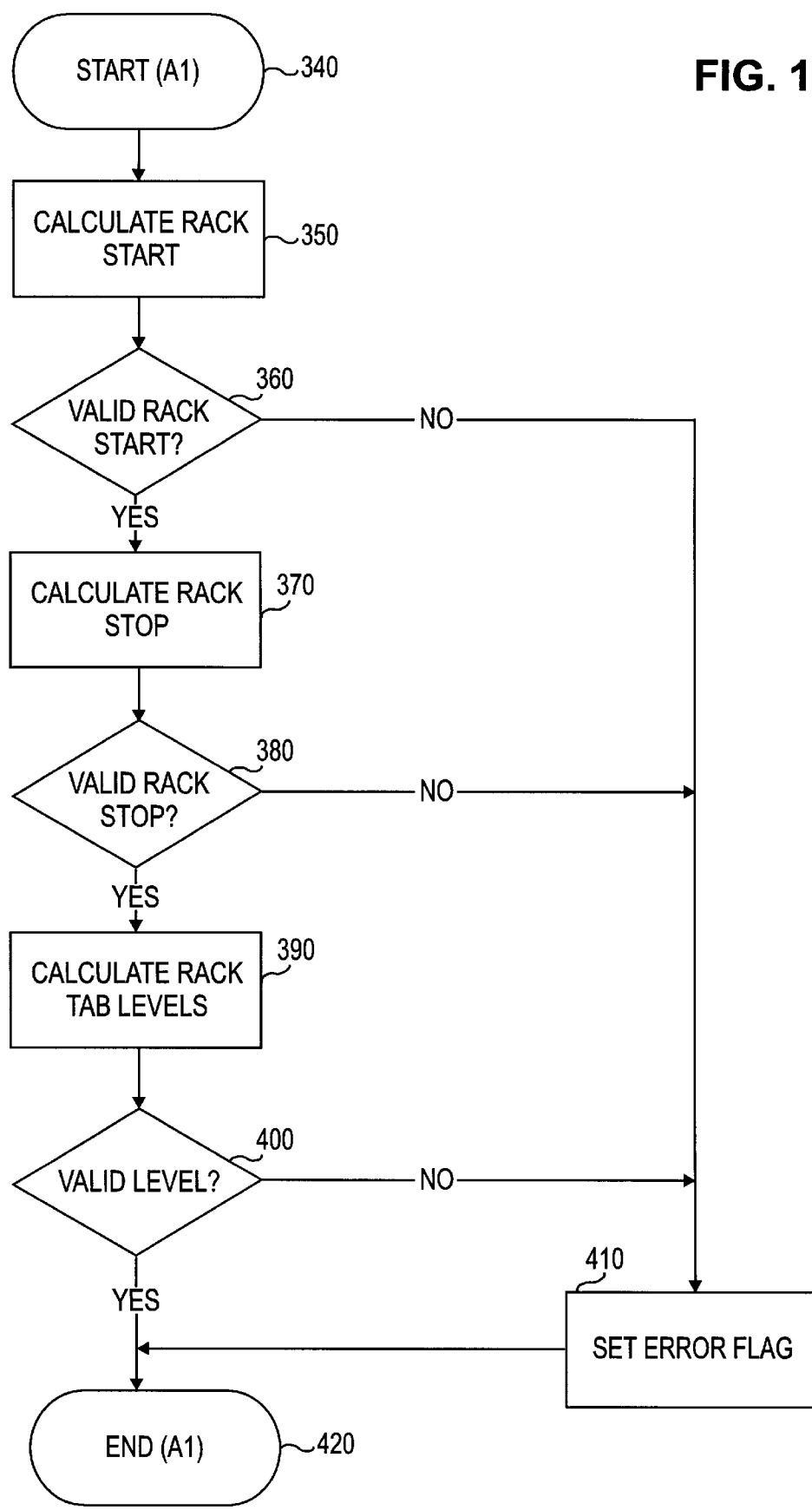
FIG. 12 is a flow chart of an algorithm for calculating the beginning and ending points of the rack from the first echo (step 240 of the algorithm of FIG. 11)

After the data is compiled in the FIFO buffer, the formatted data is then sent to sample handler controller where it is processed. It is checked at step 230 to determine whether the captured data is valid. This requires checking that there are enough points to span the whole rack 70 of information and that the values of the captured data are in the region of interest, basically between 0 and 6 inches. If the data is invalid, an error flag is set at step 310, and the algorithm is ended at step 330. If the data is valid, the controller proceeds to step 240 where the starting and stopping points of the rack 70 (i.e., the beginning and end of the racks) is calculated by looking at data from the first echo using algorithm A1 shown in a flow chart in FIG. 12. At step 250, the system checks whether the calculated starting and stopping points are valid by checking that there are approximately the number of data points in the length of the data stream expected to be generated by the rack 70. This insures that the rack was transported under sensor 90 at approximately the correct speed to have obtained the number of points needed to accurately determine a particular feature of the rack and containers. If the starting point and ending point are at acceptable levels for tabs 76a, 76b, the points are determined to be valid and the system proceeds to step 260. Otherwise, the starting and stopping points are not valid, and the system proceeds to step 310 where the error flag is set.

In algorithm A1, which starts at step 340, these starting and stopping points of the rack 70 are calculated based on a change in signal level from the background level, when the ultrasonic burst is reflected back from the bottom of cross-feed 95 (beneath track 102), to a level of the tabs 76a, 76b on the rack 70. This helps to determine the length of the rack 70 in the overall data stream. At step 350, since tabs 76a, 76b on racks 70 are, in the preferred embodiment, approximately 14 mm long, the data is analyzed to look for a region where there is a steady level of data for approximately 30 data points in a first area of interest where tabs 76a, 76b should be, which is between approximately 3 and 3½ inches above the background level. By checking for 30 points, the software does not mistakenly identify the top surface of a rack 70 between tube receptacles 72, as being a tab because the distance between tube receptacles 72 is only 2.5 mm. If there is a steady level of data at the appropriate level, the data point where the change in levels to a steady level begins is set to be the rack start position lengthwise on the rack 70. The validity of the rack start position is verified at step 360. If there is no steady level of data or if the data is not within the first two inches, then the error flag is set at step 410. At step 370, the rack stop position is calculated by looking for a second length of data at a steady level for approximately 30 points at the appropriate height between approximately 3 and 3½ inches above the background level.

At step 380, it is determined whether the calculated rack stop is valid. Because a rack start position has already been determined and because all of the racks 70 are supposed to be approximately the same length, the rack stop position should be at a known distance from the rack start position. If the rack stop position is not the distance from the rack start position where it should be, if there is no second steady level of data, or if the first and second steady levels of data are not within 228 mm from one another, the calculated rack stop is invalid and the subroutine proceeds to step 410 where the error flag is set. If the calculated rack stop position is valid, at step 390 the rack start and stop data is used to calculate the rack tab levels from the steady levels of data. The average value of the 30 data points beyond the leading edge of the rack start position is initially computed and this average is then recomputed by throwing out any of the 30 data points that are more than 5% different from the initially computed average. This latter value, the recomputed average, is set as the rack tab level for the start tab 76a. Similarly, the average value of 30 data points before the trailing edge is initially computed and this average is then recomputed by throwing out ("outliers"), i.e., any of the 30 data points that are more than 5% different from the initially computed average. This latter value is set as the rack tab level for the stop tab 76b. The data points that define the tab area are now changed in the FIFO buffer to equal the average value. All measurements of the inner and outer diameter of the containers and the liquid levels of the containers are thereafter calculated with respect to these levels.

At step 400, the reference level of the start and stop tabs 76a, 76b may be checked again to insure that the tabs 76a, 76b are at valid levels. This involves checking that the levels are at an appropriate height, which must be within 5 to 8 mm of the top of the rack 70, and that the start and stop tab levels are within 5 mm of one another. The first and second steady levels of data should be the same but the rack 70 may not be properly seated in cross-feed 95, causing the rack 70 to sit at an angle with one tab sitting higher than the other tab. If the rack tab levels are not valid, the error flag is set at step 410. If the rack tab levels are valid, the algorithm of FIG. 12 ends.

Echoes may be lost because they arrive too early at sensor 90, before the "Window Open" condition, or they arrive too late, after the "Window Close" position resumes. On an echo may be lost if reflected off a surface in the dead zone. An echo may also be lost when the object on which the ultrasonic burst impinges absorbs the burst and reflects at most a small undetectable echo, such as where there are bubbles 38 on the surface of a liquid in a container 36, as shown in FIG. 5(a). Yet another situation where an echo may be lost is where either the top of the container is too high because the container is not properly seated all the way down in the rack 70 or where the container in the rack 70 is too high to be used within the instrument.

The echo may arrive too late, i.e., after the "Window Close" condition, when the burst is deflected over the length of a container such that the echo must travel over a longer distance than should be necessary. This lost echo condition may be caused by the misalignment of sensor 90 and the detector away from the proper orientation, when ultrasonic burst hits a curved piece on a container, or, as shown in FIG. 5(b), from a meniscus 43 which has formed on the top surface of the liquid sample in container 40 where, for example, there is a low surface tension. In this latter case, a first echo 42 may be detected but a second echo 44 is lost because it bounces between the side walls of container 40 and takes too long to return to the sensor.

Figure 8:
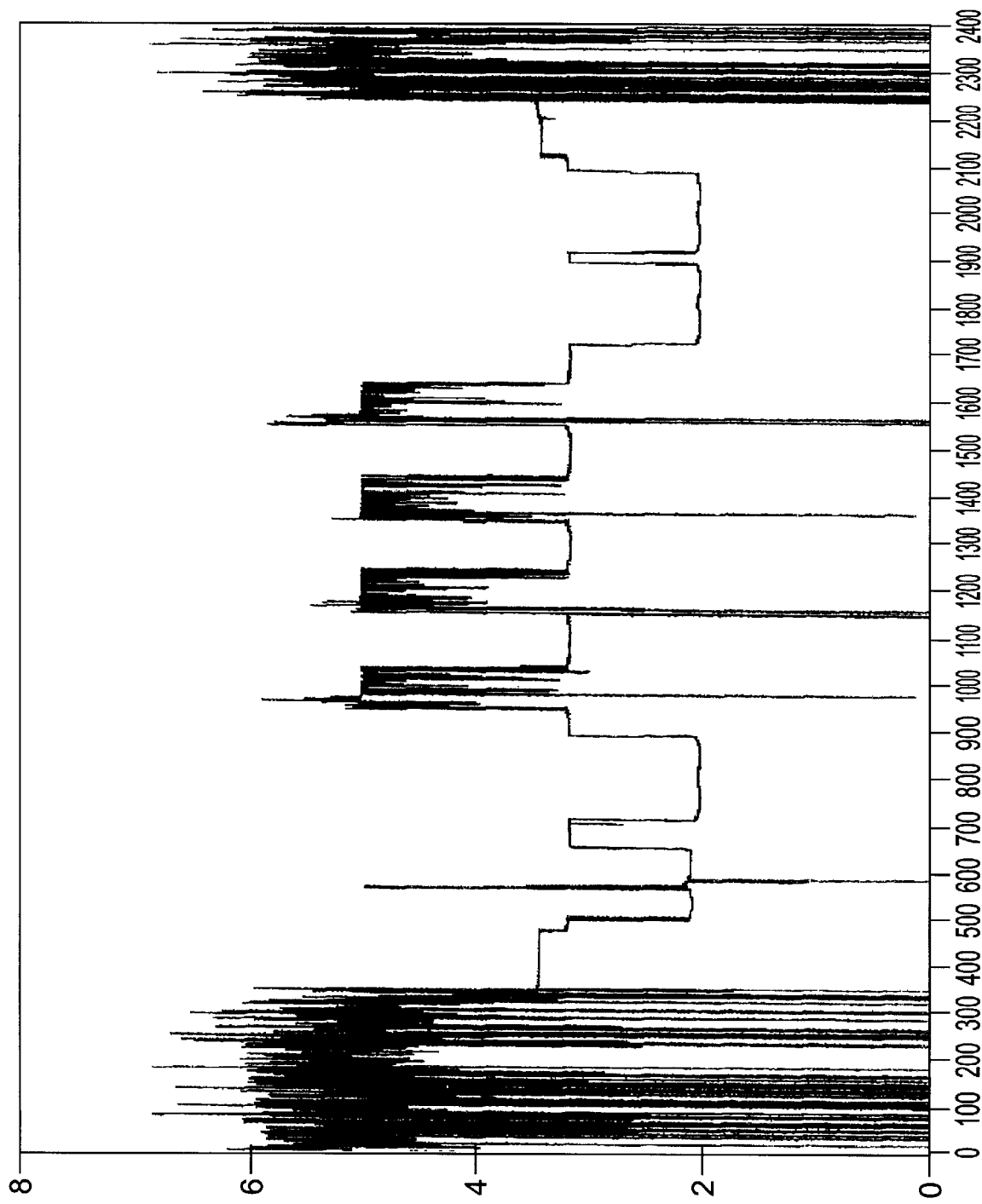
FIG. 8 is a graph of the profile of additional raw data.
Figure 9:
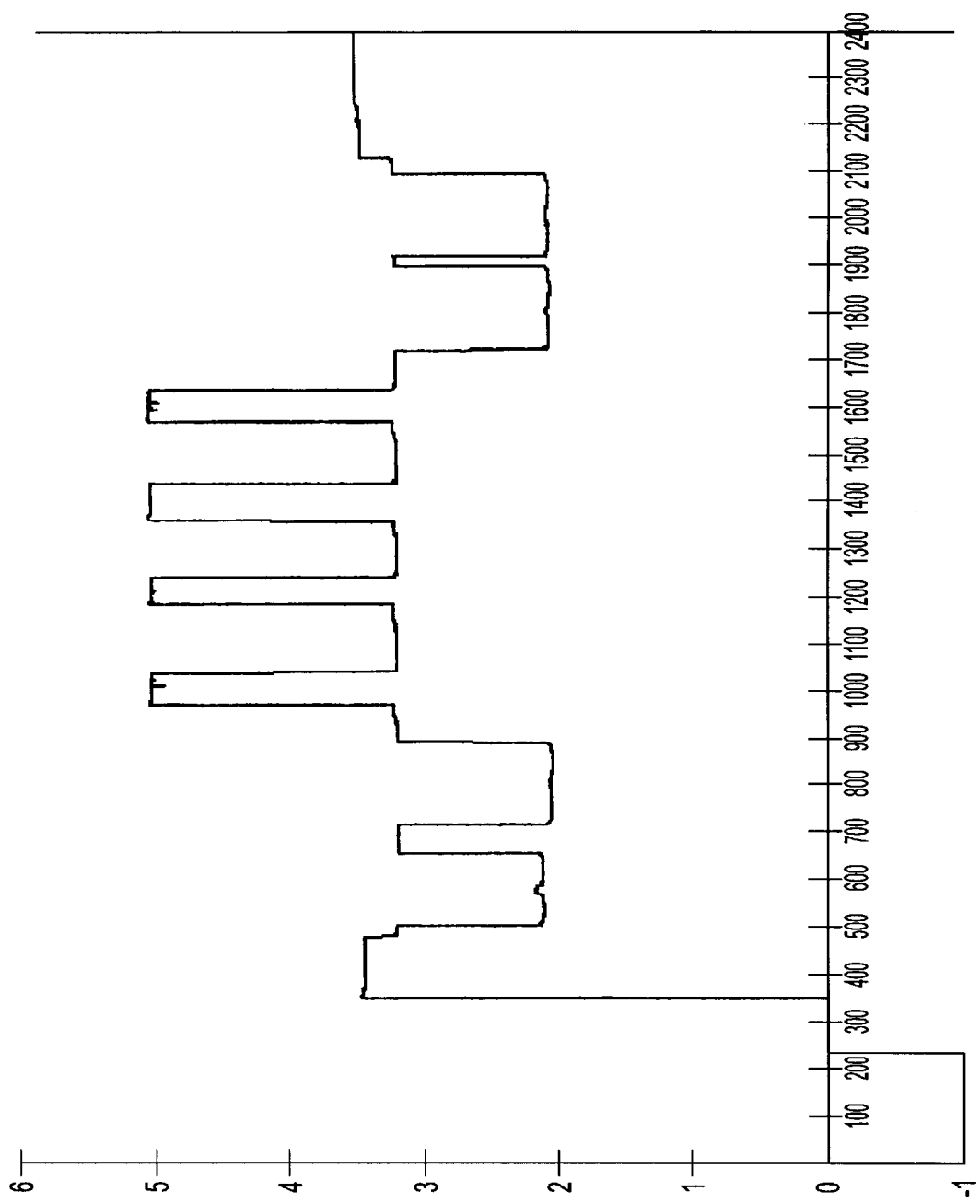
FIG. 9 is a graph of the profile of the raw data of FIG. 8 after a first filter has been used to filter the large spikes in the raw data.

The lost echoes generate large spikes in the data, such as the large spike visible, for example, in FIG. 8. To filter out noise introduced by lost echoes, referred to as Noise Level I in the flow chart, at step 260, the spikes generated by the lost echoes are discarded. Each spike is replaced with the last good data in the incoming data stream. For example, the filtered data of FIG. 8 is shown in FIG. 9.

At step 270, after the data has been filtered, the level of a reference plane for the rack is determined by plotting a straight line between the start tab reference level and the end tab reference level.

At step 280, the data for the start and stop tabs 76a, 76b is again checked to insure that the start and stop tabs 76a, 76b are still in the correct range of approximately 3 to 3½ inches away from sensor 90 despite the filtering. If the levels are no longer valid, then the algorithm advances to step 310 where the error flag is set. If the levels are still valid, the algorithm advances to step 290 where a second noise filter for Noise Level II for small spikes is applied to the data previously filtered through the filter for Noise Level I. Small spikes, such as those shown in FIG. 7A, are generated by surrounding electronics, e.g., greater than 2 mm above the background noise of the system, and must be smoothed in the regions of the rack tabs 76a, 76b and the tops of the containers. The data is thereby flattened to obtain a good estimate of the height of the container and rack. This filter requires two parameters to be programmed into the workstation software: the noise tolerance value and the continuous tolerance value. The noise tolerance value controls how much a particular data point may deviate from its previous neighboring data point. The continuous tolerance value of 5 points controls how much a data point may deviate from other adjacent data points in a larger neighborhood of data surrounding the data point under consideration. In a preferred embodiment, the noise tolerance value for a particular data point is examined by looking to the 4 adjacent data points, including the 2 data points that precede and the 2 data points that follow the data point under consideration. If the noise tolerance value is exceeded, the value of the data point is compared to the value of the adjacent 4 points. If the data point under consideration exceeds the average value of the adjacent 4 points by more than the continuous tolerance value, the value of the data point under consideration is set to the average value of the adjacent 4 data points. In a preferred embodiment, the noise tolerance value is 2.5 mm (approximately 0.1 inches) and the continuous tolerance value is 1 mm (approximately 0.05 inches).

Figure 13:
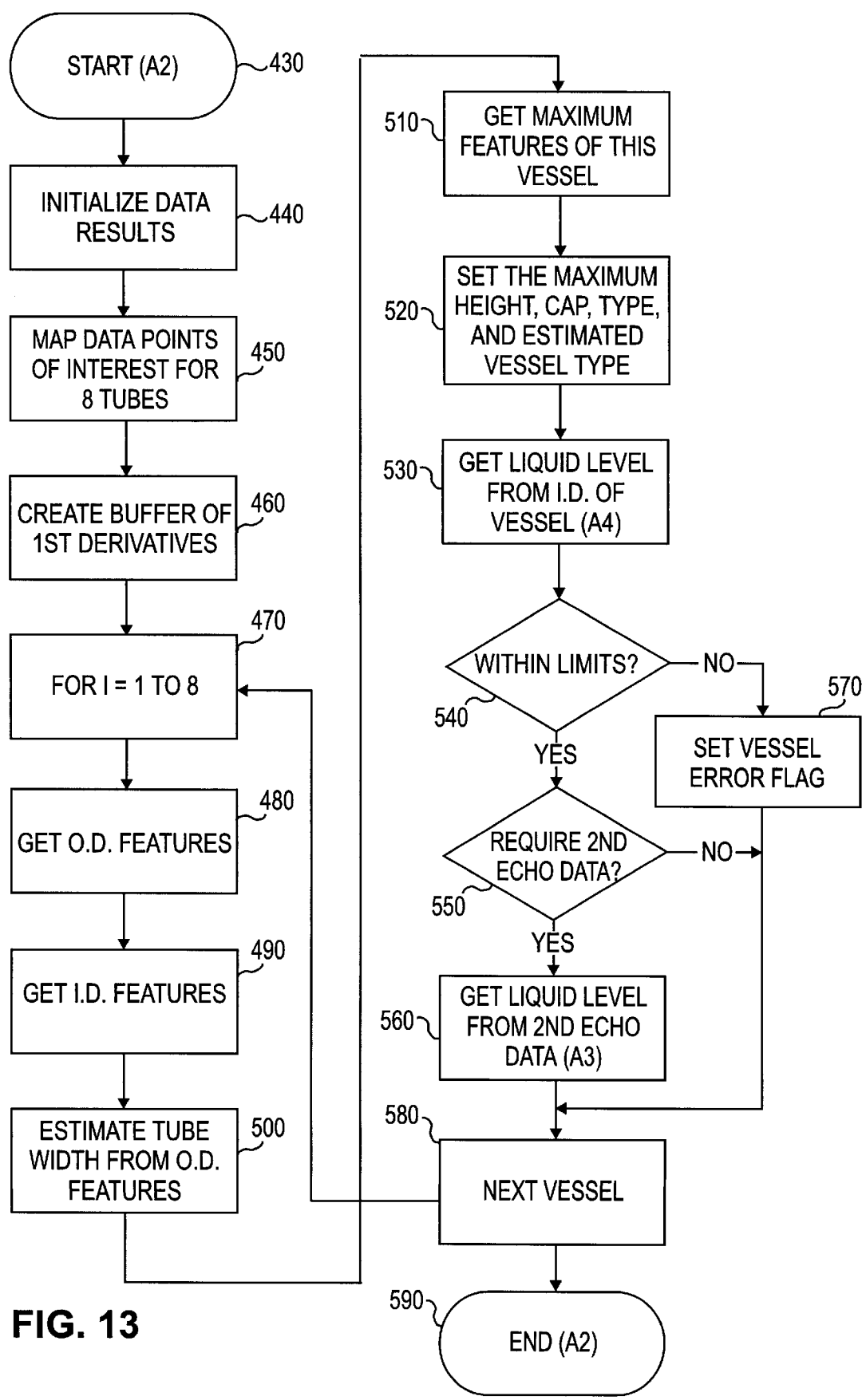
FIG. 13 is a flow chart of an algorithm for calculating the height, liquid level and container type from the ultrasonic profile shown in FIG. 11 (step 300 of the algorithm of FIG. 11)

After the filtering for Noise Level II has been completed, the routine advances to step 300 where the height of each container above the reference plane, defined by the top of the rack, and the container types are determined, and, if the containers are determined not to have caps, the level of liquid in the containers is also determined. The details of the algorithm A2 for performing step 300 are shown in FIG. 13 starting at step 430. At step 440, the data results are initialized by setting all containers to invalid. Next, at step 450, points of interest from the eight or fewer containers in the rack 70 are mapped from the filtered data of FIG. 9 to "rough out" the areas which are analyzed to determine the features of the containers. These points of interest are mapped for all 8 locations on the rack, regardless of whether or not a container is present in any of the locations. These areas are determined by knowing the start and stop points of the rack 70 computed earlier, the speed with which the rack 70 travels in cross-feed 95, and the approximate number of data points that should have been collected for each container.

After the points of interest for the 8 containers have been mapped out, at step 460, the first derivative of the change in the measured level from a first data point to a second adjacent data point with respect to the time elapsed between the two readings is calculated for each data point in the entire data stream and stored in a buffer. The derivatives reflect transitions indicating either the start of the outer diameter of a container or the start of an inner diameter of a container. The transitions thereby provide the information that indicates where to look for the liquid level whether or not the container types are identified.

With the transitions identified, the software enters a loop at step 470, which includes steps 480–580. The loop is repeated eight times to analyze the features of the eight containers one container at a time. Starting with the first container, at step 480, the outer diameter features of the first container, i.e., the width, are identified using the first derivative. At step 490, the inner diameter features are identified, if these features are identifiable because there is no cap on the container. If the container is capped, there will be no discernable inner diameter. At step 500, using the outer diameter features, the container width is estimated, although this estimate is not reliable because of container variation, detector beam variation and beam alignment and so is not used to determine the container type. With the container width known, the maximum height of the container at step 510 equals the first derivative taken at the two outer diameter points of the particular container. The maximum height of the container is, in turn, used to determine whether the container is capped and the container type.

Figure 15:
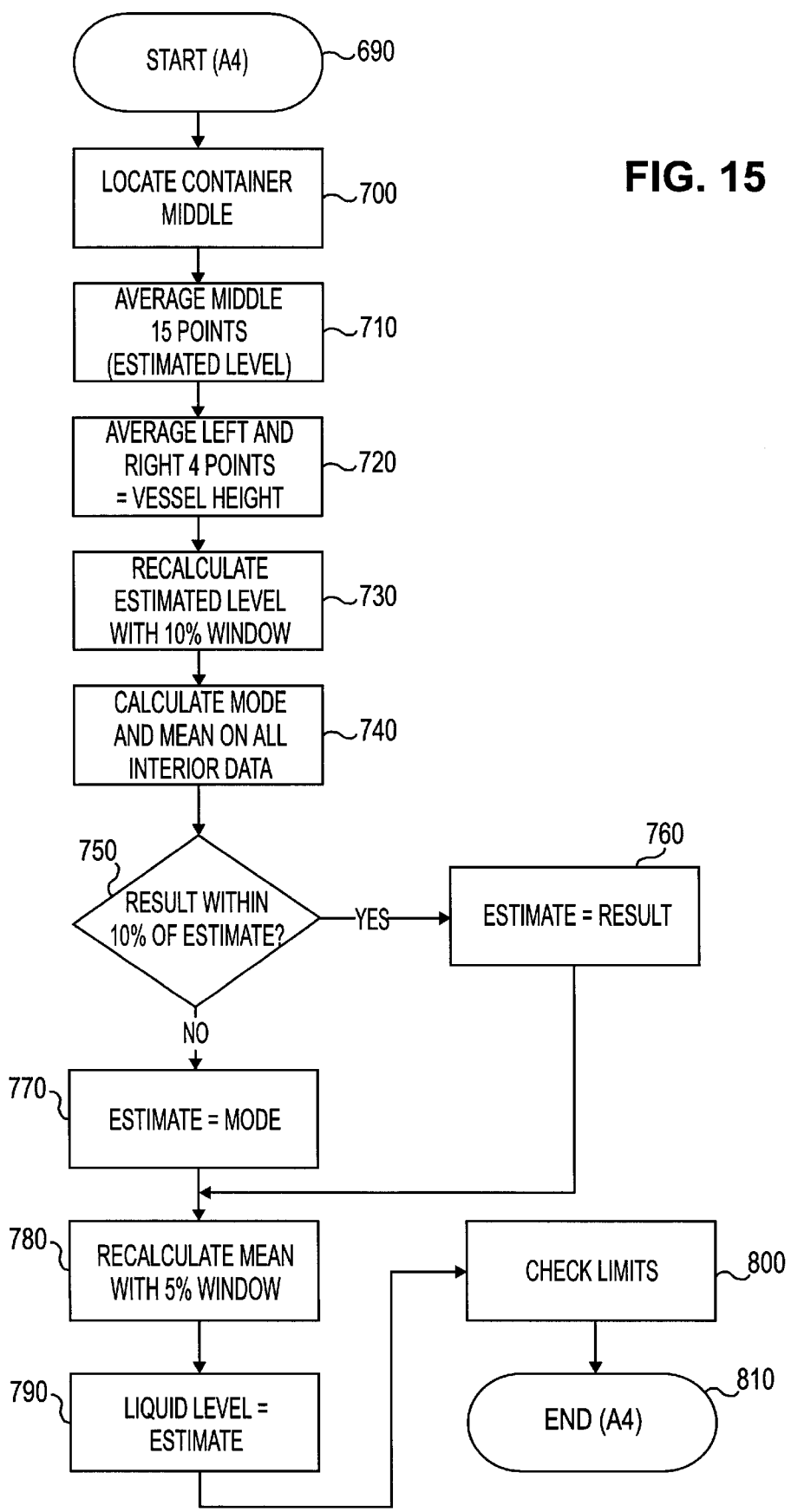
FIG. 15 is a flow chart of an algorithm for obtaining the liquid level after identification of container type (step 530 of FIG. 13 and step 640 of FIG. 14)

In addition to the maximum height, the approximate height of the container is computed based on the measured level of the inner features of the container above the reference rack level and is used to verify the type of container and to determine whether the container is seated correctly. To compute the approximate height, an algorithm determines the average level in the vicinity of the lip of the container and filters the data by throwing away outliers (i.e., recomputes the average to disregard those data points that are more than 5% different from the initially computed average level) and recalculates what it thinks the height of the container is. The algorithm thereby determines the form of the lip height of the container. The level of the lip of the container is set as the maximum height of the container at step 520. If the measured level of the lip rises above the container within the area of the lip, it is verified that the container is capped and the type of cap is identified by the height of the data points across the container. Also estimated at step 520 is the container type based on the height and diameter of the container.

Where a container is determined from the derivatives computed for the first echo to have a measurable inner diameter, this means that there might be liquid in the container, the level of which may be measured. The liquid level for a container having a measurable inner diameter is determined at step 530 using algorithm A4 (FIG. 15). In algorithm A4, which starts at step 690, the middle of the container is located in step 700 using the middle point between the points that identify the inner diameter of the container. The estimated level is taken by taking an average of the middle point and 7 points on either side of the middle point (step 710). Also computed, at step 720, is the vessel lip height by taking the average of all of the interior data points between the outer diameter and inner diameter of the container using the level of the left 4 points minimum and the right 4 points minimum because each set of 4 points represents the thickness of the glass wall of a typical container. For a container with thicker or thinner walls, additional or fewer points, respectively, will be used to calculate the vessel lip height. The average level computed in step 720 is the "Vessel Height." At step 730, it is determined whether the estimated level of the middle 15 points, calculated at step 710, is less than 10% different from the Result computed in step 740. If it is within 10%, then the estimated level is reset to equal the Result. The mode and mean of all of the interior data (i.e., data points between the inner diameter of the container) are calculated at step 740. If the mode and mean are with 10% of the estimated level (meaning the value after step 730) then the estimated level is reset equal to the Result and the algorithm proceeds to step 780. If the mode and mean are not within 10% of the estimate, (which may be because a meniscus is formed on the surface of the liquid and the liquid level measured by the various data points varies between a low liquid level at the center of the container to a high liquid level away from the center), then the estimated level is reset to equal the mode (step 770).

At step 780, the mean is recalculated using the mode as the estimated level set in either of steps 760 and 770. If the mean is within 5% of the estimated level, then the liquid level equals the estimate. Otherwise, the liquid level is set equal to the mean. At step 800 the calculated liquid level is compared to the liquid level limits for the identified type of container.

At step 540, the calculated liquid level is analyzed to determine if the liquid level is within the allowed limits. If the liquid level is not within the allowed limits, i.e., the amount of liquid is too large for the container type previously determined or is too low, an error flag is set for that container at step 570 and the data for the next container, if any, is analyzed starting at step 480. If the liquid level is within the allowed limits, the algorithm next determines at step 550 whether, based on the maximum features of the container and the measured liquid level, the liquid level has not been properly measured with data from the first echo. The liquid level is not generally properly measured if the container type appears to be a container with an insert because the small opening of these containers produces a measured height equal to the height of the outer lip of the container.

Inserts are present where the measured height of the outer diameter of the container is 77 mm (which identifies an EZEE-NEST insert in a 75 mm VACUTAINER tube) or 96 mm (which identifies a sample cup in a MICROTAINER holder). In this situation, such as with containers D, E and G of FIG. 7A and containers J–Q of FIG. 7B, the liquid level is not determinable from the first echo, and the second echo is analyzed at step 560 to determine the liquid level. Because sensor readings vary +/−1 mm and it is therefore difficult to distinguish VACUTAINER containers that are 75 mm in height and do not have an Ezee Nest® insert from those containers that do have the insert, it may be necessary to use the second echo to determine the liquid level of 75 mm VACUTAINER containers even though the liquid level data is ascertainable for these VACUTAINER containers from the first echo. Any remaining second echo data that is not required to determine the liquid level is discarded.

Figure 14:
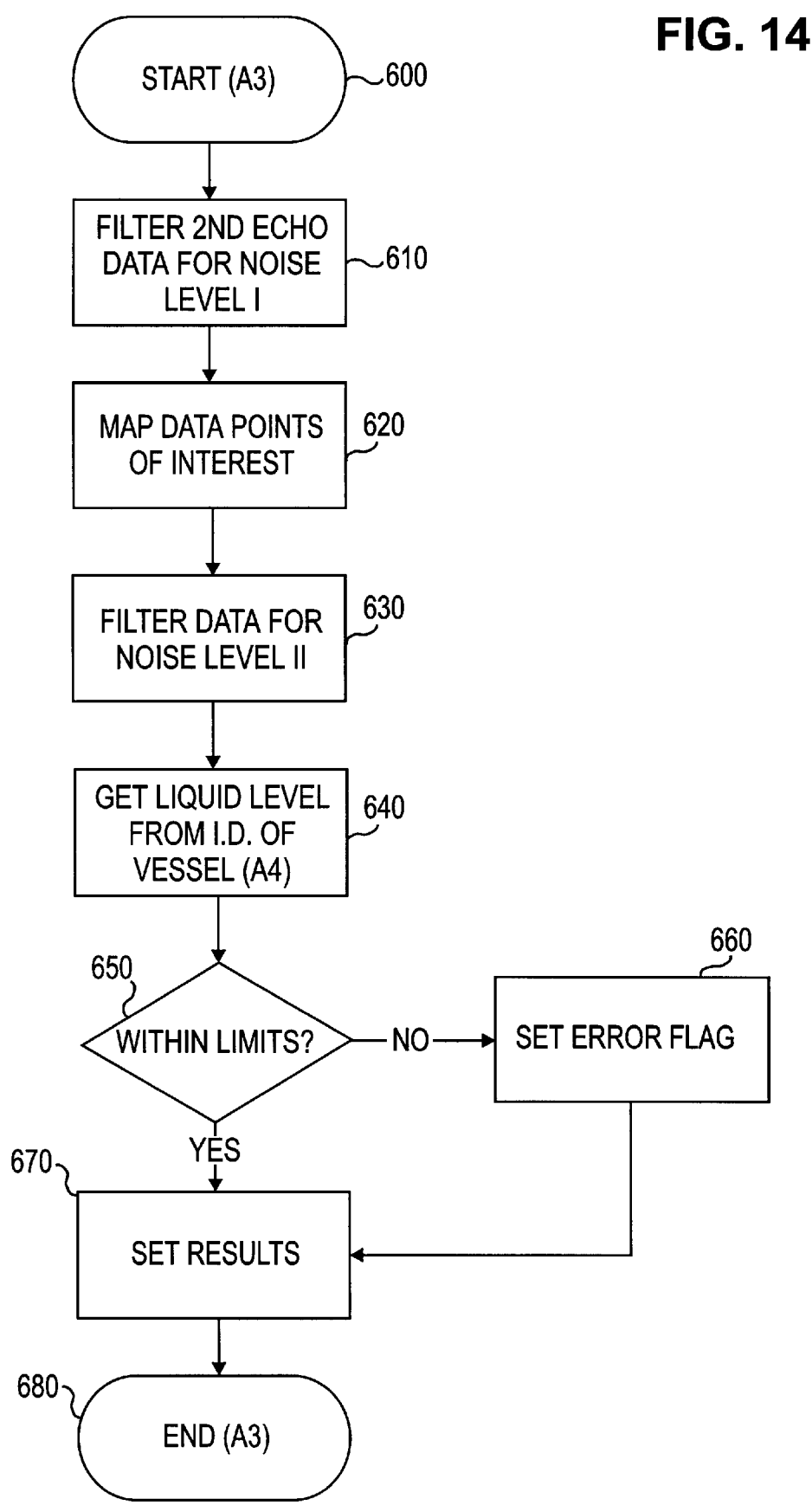
FIG. 14 is a flow chart of an algorithm for filtering the second echo data, when necessary, to obtain the liquid level (step 560 of FIG. 13)

The details of step 560 are shown in a flow chart in FIG. 14 and referenced as algorithm A3, which starts at step 600. As with the first echo data, the second echo data is filtered at step 610 for Noise Level I, using the same technique used in step 260 to eliminate large spikes of noise resulting from lost echoes but applying it to the second echo data. At step 620, the data points of interest, which in this instance means that the containers that have inner diameters that are types for which a liquid level must be determined from the second echo, are mapped. The remaining data points, if any, in the second echo are disregarded. At step 630 the data points are filtered for Noise Level II consisting of small noise spikes in the liquid level wells using the same technique described with respect to step 290. At step 640, using the algorithm A4 shown in FIG. 14 and described above, the liquid level is determined by smoothing and averaging the data points within the inner diameter of the container, by using an estimated value of the liquid level and then recalculating the liquid level by throwing out the outliers (i.e., recomputed the average level by disregarding in the computation those data points that differ more than 5% from the initially computed average) from the inner diameter of the container. At step 650, the liquid level calculated at step 640 is analyzed to determine if the liquid level is within an allowed liquid level, and, if so, the liquid level is set to the calculated value. If it is not an allowed liquid level, the error flag is set at step 660. If the liquid level is within the limits, the liquid level is confirmed and is set at step 670. The algorithm of FIG. 13 then ends at step 680 and returns to step 580 of algorithm A2 if there are any further containers to be analyzed. After the further containers are analyzed, algorithm A2 ends at step 590.

Once the height, tube type and liquid level of the containers are determined, the results are sent to the system processor at step 320, and the algorithm ends at step 330.

Instrument should be operable at least within an environment where the approximate temperature is within the range of 15–35° C. Because the speed of sound varies 1% for each temperature change of 10° C., data acquisition board periodically measures the temperature during the profiling of the containers using an on-board temperature sensor and compensates for any temperature change by utilizing a correction constant in converting the measurement of the time necessary for the ultrasonic burst to travel into a distance measurement. This temperature compensation feature is built into the Cosense data acquisition board and is understood by those skilled in the art.

To insure the accuracy of the data, even where not explicitly prescribed, whenever an average value is calculated above, it is preferable to calculate the estimated value, the mean value, and the mode. All of these three values must be close, or else the data point is thrown out as invalid.

In all circumstances, if the container type cannot be determined after analyzing a region of interest of approximately 200 points, the container is rejected as unrecognizable. The rejected container is not extracted by the robotic arm for transport elsewhere in instrument and the container left in the rack when the rack is output into outfeed 100.

Capped test tubes may be sent to an automatic decapper where the cap is removed and another ultrasonic liquid level sensor sitting above the container in the decapper detects the liquid level after the cap is removed. Moreover, if the data suggests that the container is an uncapped container but the liquid level in the container is too high, the container may be extracted by the robotic arm and transported to an external device where the robotic arm seats the container properly. This external device may be the automatic decapper referenced above.

The containers to be profiled may be input on an identical or similar rack placed on stat shuttle 85. The rack is transported at a slew speed under ultrasonic sensor 87, which is preferably identical to sensor 90 and operated in the same manner as sensor 90, including the same frequency and pulse width. Moreover, if one or more containers were not properly processed by sensor 90, meaning either no results or incorrect results were obtained, the robotic arm may transport the container to a test tube rack on stat shuttle 85, which may be nearly identical to cross-feed 95 and which has another ultrasonic liquid level sensor 87, preferably identical to sensor 90. To place the test tube in the rack, the rack on stat shuttle 85 must be within the reach of the robotic arm. Where the robotic arm only reaches the rear area of the stat shuttle 85, the test tube rack is output to the front area of stat shuttle 85 and the rack is then transported back to the rear area. The rack thus passes under sensor 87, where another attempt may be made to properly profile the container.

The described system captures data in the data acquisition board 98 and sends the data to the sample handler controller for processing. However, to increase the processing speed of the data, it is preferable to modify the board 98 to provide sufficient processing speed for processing the data and memory for loading on-board control software.

Figure 16:
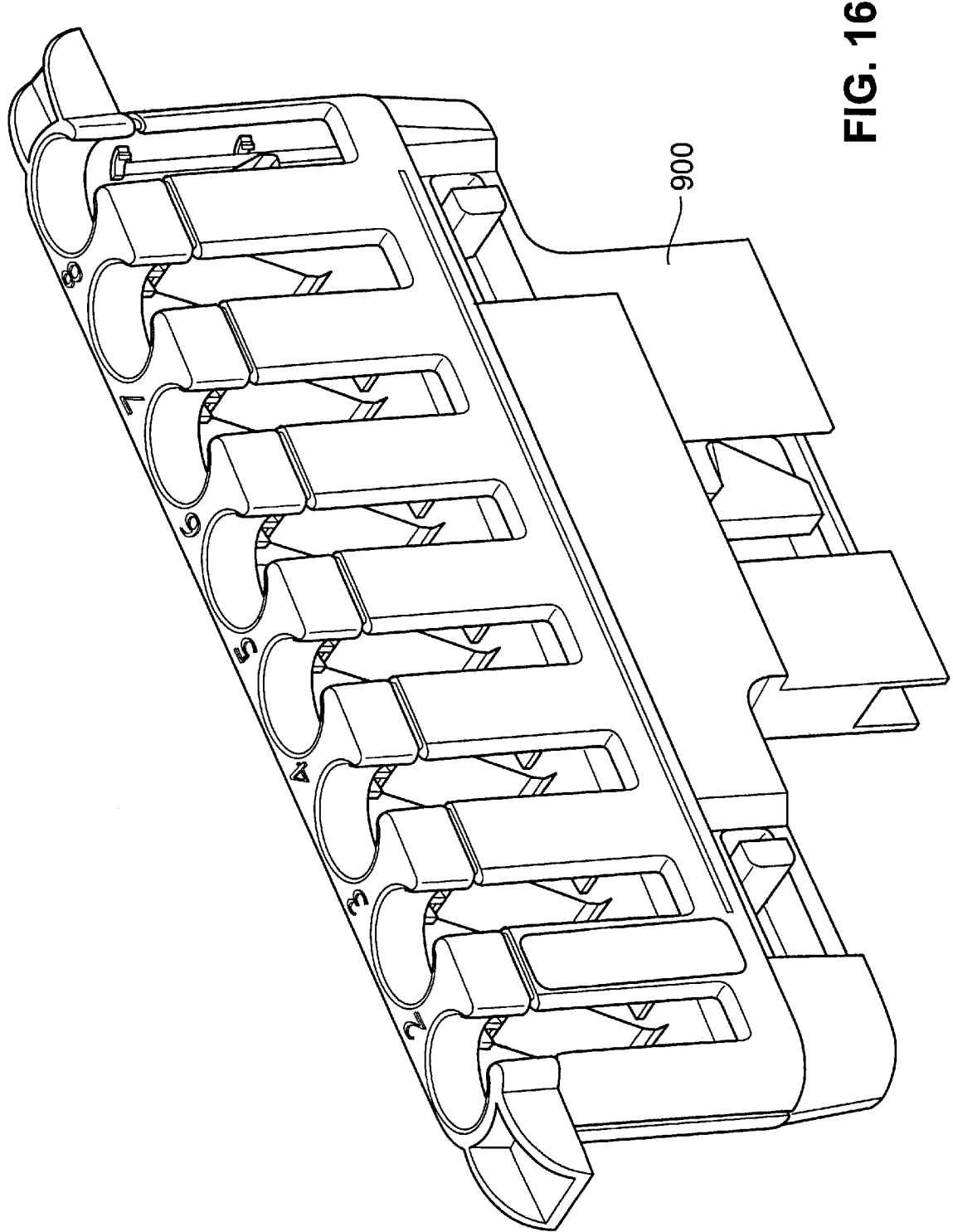
FIG. 16 is an isometric view of a second embodiment of a rack with which this invention may be used.

One skilled in the art will recognize that the present invention is not limited to the above-described preferred embodiment, which is provided for the purposes of illustration and not limitation. Modifications and variations may be made to the above-described embodiment without departing from the spirit and scope of the invention. It should be recognized that the invention is not limited to the described sample handler or racks. For example, FIG. 16 shows a rack 900, which is another embodiment of a rack that may be transported past ultrasonic sensor 90 on cross-feed 95 when the analytical instrument is operated in a laboratory automation mode described in the referenced Sample Handler application.

We claim:

1. A method of dynamically profiling a container in a rack in an apparatus having an ultrasonic sensor, said method comprising the steps of:

moving said rack within and through a sensing range of said sensor;

transmitting a plurality of ultrasonic bursts from said sensor toward said rack as said rack is moved past, and within said sensing range of, said sensor;

detecting a plurality of echoes from said plurality of ultrasonic bursts striking said container and said rack;

generating a plurality of data points from said detected plurality of echoes; and profiling said rack using said plurality of data points to determine information about said container.

2. The method of claim 1 wherein said profiling comprises using said plurality of data points to determine said type of said container.

3. The method of claim 1 wherein said profiling comprises using said plurality of data points to determine whether said container is capped, and, where said container is not capped, determining a liquid level in said container.

4. The method of claim 1 wherein said rack has start and stop tabs and said container has a height, and said step of profiling comprises calculating a rack reference level from a first subset of said plurality of data points, said first subset reflecting a location of said start and stop tabs in said plurality of data points, and calculating said height of said container using said rack reference level.

5. The method of claim 4 further comprising calculating said start and stop points of said rack, and determining said information about said container from a second subset of said plurality of data points, said second subset reflecting a location of said container in said rack.

6. The method of claim 1 wherein said detection of said echoes comprises detecting first and second echoes.

7. The method of claim 6 further comprising determining said type of container using said first echoes, and determining a liquid level of a sample in said container using said second echoes, where said first echoes do not provide said liquid level for said type of container and said container is uncapped.

8. The method of claim 1 wherein said profiling comprises filtering said plurality of data points to modify those of said data points reflecting lost echoes.

9. The method of claim 1 further comprising operating said sensor as a short range sensor.

10. The method of claim 9 wherein said sensor is operated at a frequency of approximately 1 MHz.

11. The method of claim 1 wherein said step of moving said rack comprises moving said rack at a slew speed.

12. A method of profiling a container in a rack in an apparatus having an ultrasonic sensor, said method comprising the steps of:

transporting said rack within a sensing range of said sensor;

transmitting an ultrasonic burst from said sensor toward said rack as said rack is transported past, and within said sensing range of, said sensor; and detecting at least two echoes from said burst striking said container and said rack.

13. The method of claim 12 wherein said step of transporting said rack comprises transporting said rack at a slew speed.

14. An apparatus for dynamically profiling a container in a rack comprising:

an ultrasonic sensor having a first output corresponding to an emitted acoustic signal and a second output corresponding to an electrical signal representing echoes in response to said first output, a rack transport mechanism positioned relative to said ultrasonic sensor to move said rack relative to said sensor, and a processor responsive to said second output to profile said rack and determine the type of container, and liquid level therein.

15. The apparatus of claim 14 wherein said first output comprises a plurality of ultrasonic bursts.

16. The apparatus of claim 14 wherein said first output comprises a plurality of ultrasonic bursts emitted at a frequency of approximately 1 MHz.

17. The apparatus of claim 15 wherein said rack transport mechanism comprises a means for moving said rack at a slew speed.

18. The apparatus of claim 14 wherein said processor further comprises processing means for generating a plurality of data points from said second output and creating a profile of said plurality of data points; and a memory device to capture said plurality of data points.

19. An apparatus for profiling a rack containing at least one capped tube and one open tube comprising processing means for executing an algorithm to profile said tubes in said rack, said profiling algorithm including determining a tube type, whether said tubes are capped or open, and, for those of said tubes that are open, a liquid level of a sample in said tubes.

* * * * *